(12) United States Patent
Williams et al.

(10) Patent No.: US 10,654,785 B2
(45) Date of Patent: May 19, 2020

(54) CONVERSION OF CORN OIL TO UPGRADED BIODIESEL AND POLY(LACTIC ACID)

(71) Applicant: UNIVERSITY OF SOUTHERN CALIFORNIA, Los Angeles, CA (US)

(72) Inventors: Travis J. Williams, Los Angeles, CA (US); Zhiyao Lu, Duarte, CA (US); Valery Cherepakhin, Los Angeles, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 16/193,590

(22) Filed: Nov. 16, 2018

(65) Prior Publication Data

US 2019/0144369 A1 May 16, 2019

Related U.S. Application Data

(60) Provisional application No. 62/587,299, filed on Nov. 16, 2017.

(51) Int. Cl.
*C07C 51/09* (2006.01)
*C10L 1/02* (2006.01)
(Continued)

(52) U.S. Cl.
CPC .......... *C07C 51/09* (2013.01); *B01J 31/2295* (2013.01); *C07F 17/02* (2013.01); *C10L 1/026* (2013.01);
(Continued)

(58) Field of Classification Search
CPC .......... C07C 51/09; C07F 17/02; C10L 1/026; C10L 2200/0476; C10L 2270/026
(Continued)

(56) References Cited

U.S. PATENT DOCUMENTS

2017/0014817 A1   1/2017   Williams et al.
2017/0217870 A1   8/2017   Williams et al.

OTHER PUBLICATIONS

Chadwick, F.M. et al., "A convenient route to norbornadiene adduct of iridium with chelating phosphines, [Ir(R2PCH2CH2PR2)(NBD)][BArF4] and a comparison of reactivity with H2 in solubon and solid-state," J. of Organomet. Chem. 2016, 812, pp. 268-271.
(Continued)

*Primary Examiner* — Deborah D Carr
(74) *Attorney, Agent, or Firm* — Brooks Kushman P.C.

(57) ABSTRACT

Conversion of vegetable-derived triglycerides to fatty acid methyl esters (FAMEs) is a popular approach to the generation of biodiesel fuels and the basis of a growing industry. Drawbacks of the strategy are that (a) the glycerol backbone of the triglyceride is discarded as waste in this synthesis, and (2) many natural triglycerides are multiply-unsaturated or fully saturated, giving inferior performance and causing engine problems with long-term use. Here, we show that catalysis by iridium complex 1 can address both of these problems through selective reduction of triglycerides high in polyunsaturated fatty esters to FAMEs with high oleate concentration. This is realized using hydrogen imbedded in the triglyceride backbone, concurrently generating lactate as a value-added $C_3$ product. Additional methanol or glycerol as a hydrogen source enables reduction of corn and soybean oils to >80% oleate.

39 Claims, 13 Drawing Sheets

(51) Int. Cl.
*B01J 31/22* (2006.01)
*C07F 17/02* (2006.01)

(52) U.S. Cl.
CPC . *C10L 2200/0476* (2013.01); *C10L 2270/026* (2013.01)

(58) Field of Classification Search
USPC .......................................................... 554/144
See application file for complete search history.

(56) References Cited

OTHER PUBLICATIONS

Cabral, F.J. et al., "Global Biofuel Production and Poverty in Senegal," Econ. Bull. 2017, 37 (3), pp. 1435-1449.
Celaje, J.J. et al., "A prolific catalyst for dehydrogenation of neat formic acid," Nat. Commun. 2016, 7, 11308, pp. 1-6.
Zhang, X. et al., "Ruthenium-Catalyzed Ammonia Borane Dehydrogenation: Mechanism and Utility," J. Acc. Chem. Res. 2017, pp. 86-95.
Chuah, L.F. et al., "Influence of fatty acids in waste cooking oil for cleaner biodiesel," Clean Technol. Environ. Policy 2017, 19, pp. 859-868.
Chupka, G.M. et al., "Saturated monoglyceride effects on low-temperature performance of biodiesel blends," Fuel Processing Technology, 2014, 118, pp. 302-309.
Chupka, G.M. et al., "Effect of low-level impurities on low-temperature performance properties of biodiesel," Energy Environ. Sci. 2012, 5 (9), pp. 8734-8742.
Whitfield, M.B., "Process Development for Value-Added Products from Sweet Sorghum," Dissertation submitted 2014, Biological and Agricultural Engineering, North Carolina State University, 278 pgs.
Demirbas, A., "Biofuels sources, biofuel policy, biofuel economy and global biofuel projections," Energy Convers. Manag. 2008, 49 (8), pp. 2106-2116.
Demirbas, A., "Chapter 8: Biofuel Policy," Biofuels 2009, pp. 319-329.
Fernandes, S.D. et al., "Gobal biofueld use, 1850-2000," Global Biogeochem. Cycles 2007, 21, GB2019, 15 pgs.
Gruber, S. et al., "Characterization and Reactivity Studies of Dinuclear Iridium Hydride Complexes Prepared from Iridium Catalysts with N,P. and C,N Ligands under Hydrogenation Conditions," Organometallics 2013, 32, pp. 4702-4711.
Gupta, J. et al., "Optimization of biodiesel production from mixture of edible and nonedible vegetable oils," Biocatal. Agric. Biotechnol. 2016, 8 (7), pp. 112-120.
Hamid, M.H.S.A. et al., "Borrowing Hydrogen in the Activation of Alcohols," J. Adv. Synth. Catal. 2007, 349, pp. 1555-1575.
Kant, P. et al., "The Extraordinary Collapse of Jatropha as a Global Biofuel," Environ. Sci. Technol. 2011, 45, pp. 7114-7115.
Lee, D.H. et al., Biofuel Economy and Hydrogen Competition, Energy and Fuels, 2008, v. 22, pp. 177-181.
Lu, Z. et al., "A Three-Stage Mechanistic Model for Ammonia-Borane Dehydrogenation by Shvo's Catalyst," Organometallics 2012, 31, pp. 6705-6714.
Lu, Z. et al., "A Prolific Catalyst for Selective Conversion of Neat Glycerol to Lactic Acid," ACS Catal. 2016, 6, pp. 2014-2017.
Lu, Z. et al., "Alcohol Dehydrogenation with a Dual Site Ruthenium, Boron Catalyst Occurs at Ruthenium," J. Catalysts 2012, 2, pp. 412-421.
Lu, Z. et al., "A dual site catalyst for mild, selective nitrile reduction," Chem. Commun. 2014, 50, pp. 5391-5393.
Mahmudul, H.M. et al., "Production, characterization and performance of biodiesel as alternative fuel in diesel engines—A review," Renew. Sustain. Energy Rev. 2017, 72, pp. 497-509.
Oladosu, G., "Estimates of the global indirect energy-use emission impacts of USA biofuel policy," Appl. Energy 2012, 99, pp. 85-96.
Pagliaro, M. et al., "From Glycerol to Value-Added Products," Angew. Chem. Int. Ed. 2007, 46, pp. 4434-4440.
Papadopoulos, C.E. et al., "Optimization of cotton seed biodiesel quality (critical properties) through modification of its FAME composition by highly selective homogeneous hydrogenation," Bioresour. Technol. 2010, 101, pp. 1812-1819.
Roseblade, S.J. and Pfaltz, A., "Iridium-Catalyzed Asymmetric Hydrogenation of Olefins," J. Am Chem. Res. 2007, 40, pp. 1402-1411.
Pimentel, D. et al, "Ethanol Production Using Corn, Switchgrass, and Wood; Biodiesel Production Using Soybean and Sunflower," Nat. Resour. Res. 2005, 14, pp. 65-76.
Sahoo, P.K. et al., "Process optimization for biodiesel production from Jatropha, Karanja and Polanga Oils," Fuel 2009, 88 (9), pp. 1588-1594.
Sharninghausen, L.S. et al., "Efficient selective and atom economic catalytic conversion of glycerol to lactic acid," Nat. Commun. 2014, 5, 9 pgs.
Sharninghausen, L.S. et al., "Selective conversion of glycerol to lactic acid with iron pincer precatalysts," Chem. Commun. 2015, 51, pp. 16201-16204.
Souza, B.S. et al., "Selective partial biodiesel hydrogenation using highly active supported palladium nanoparticles in imidazolium-based ionic liquid," Appl. Catal. A Gen. 2012, 433-434, pp. 109-114.
Su, M. et al., "Biodiesel production from hempseed oil using alkaline earth metal oxides supporting copper oxide as bi-functional catalysts for transesterification and selective hydrogen," Fuel 2013, 103, pp. 398-407.
Thunyaratchatanon, C. et al., "Catalytic upgrading of soybean oil methyl esters by partial hydrogenatiohn using Pd catalysts," Fuel 2016, 163, pp. 8-16.
Verendel, J. et al., "Asymmetric Hydrogenation of Olefins Using Chiral Crabtree-type Catalysts: Scope and Limitations," Chem. Rev. 2014, 114, pp. 2130-2168.
Wu, X. et al., "Optimization of biodiesel production from camelina oil using orthogonal experiment," Appl. Energy 2011, 88 (11), pp. 3615-3524.
Yang, F. et al., "Value-added uses for crude glycerol—a byproduct of biodiesel production," Biotechnol. Biofuels 2012, 5:13, 10 pgs.
Yang, R. et al., "One-pot process combining transesterification and selective hydrogenation for biodiesel production from starting material of high degree of unsaturation," Bioresour. Technol. 2010, 101, pp. 5903-5909.
Zaccheria, F. et al., "Selective hydrogenation of alternative oils: a useful tool for the production of biofuels," Green Chem. 2009, 11, pp. 462-465.

Scheme 1. General Scheme for Triglyceride Utilization

Scheme 3 showing Transfer hydrogenation by hydrogen borrowing

CONVERSION OF CORN OIL TO UPGRADED BIODIESEL AND POLY(LACTIC ACID)

CROSS REFERENCE TO RELATED APPLICATION

This application claims the benefit of U.S. provisional application Ser. No. 62/587,299 filed Nov. 16, 2017, the disclosure of which is incorporated in its entirety by reference herein.

STATEMENT REGARDING FEDERALLY SPONSORED RESEARCH OR DEVELOPMENT

The invention was made with Government support under Contract No. S10RR25432 awarded by the National Institutes of Health and Contract Nos. CHE1566167, DBI0821671, CHE0840366, and CHE1048807 awarded by the National Science Foundation. The Government has certain rights to the invention.

TECHNICAL FIELD

In at least one aspect, the present invention is related to the conversion of vegetable oils to biodiesel fuel.

BACKGROUND

The proliferation of biofuel synthesis and use presents many benefits, with U.S. biodiesel production approaching 3 billion gallons last year.[1] Key properties of the biodiesel depend almost entirely on its chemistry;[2] particularly, biodiesel that is based on triglycerides and esters of saturated fatty acids have viscosity and performance issues due to high molecular weights and melting points.[3] Thus, it is popular to convert triglycerides to fatty acid methyl esters (FAMEs). Still, FAMEs of the most popular vegetable oils in the U.S. market are polyunsaturated. This is problematic, because polyunsaturation lowers fuel energy content and lubricity and increases viscosity and gum formation. Further, fully saturated FAMEs are also undesirable due to their high melting points and reduced solubility. While full saturation and polyunsaturation in fatty acids can both cause long-term use issues, FAMEs that have high content of oleate (18:1) are an advantageous biodiesel.[3] Moreover, cleavage of the linking glycerol moiety from the triglyceride leaves this fragment, ca. 9% of the mass of the feedstock, as waste.[4]

Accordingly, there is a need for improved processes for converting triglycerides to biodiesel fuel, and in particular, to methods of converting the waste glycerol to useful products.

SUMMARY

In at least one aspect, the present invention solves the problems of the prior art by providing a method in which hydrogen is transferred from glycerol to unsaturation in the lipids from which a biodiesel can be produced.

In another aspect, a method extracting embedded hydrogen from glycerol or a compound containing functionalized glycerol is provided. The method includes a step of combining a glycerol-containing compound with a transition metal catalyst system to form a first composition. In a variation, the first composition includes a base. Characteristically, the transition metal catalyst system includes a first organometallic complex having a transition metal M. In one variation, hydrogen gas (i.e., $H_2$) is extracted from (e.g. created from) the first composition. In another variation, hydrogen is transferred to an unsaturated hydrogen receptor that includes an unsaturated moiety to form a second composition.

In another aspect, a recently reported prolific catalyst for selective conversion of glycerol to lactic acid via acceptorless dehydrogenation is utilized.[5] It is shown that with optimization, the same system can transfer hydrogen from a triglyceride backbone to its polyunsaturated fatty acids efficiently and selectively. Under the conditions set forth herein, the system reduces all linoleic acid (18:2) and linolenic acid (18:3) to oleic acid, enabling a convenient synthesis of high oleate FAMEs. This is conceptualized in Scheme 1 (FIG. 2). We further show that addition of minimal methanol and a (Macho)Fe catalyst can enable full reduction of unsaturated triglycerides while enabling direct conversion to FAME products without loss of selectivity for conversion of the backbone to lactic acid.

DETAILED DESCRIPTION

Figure 1A:
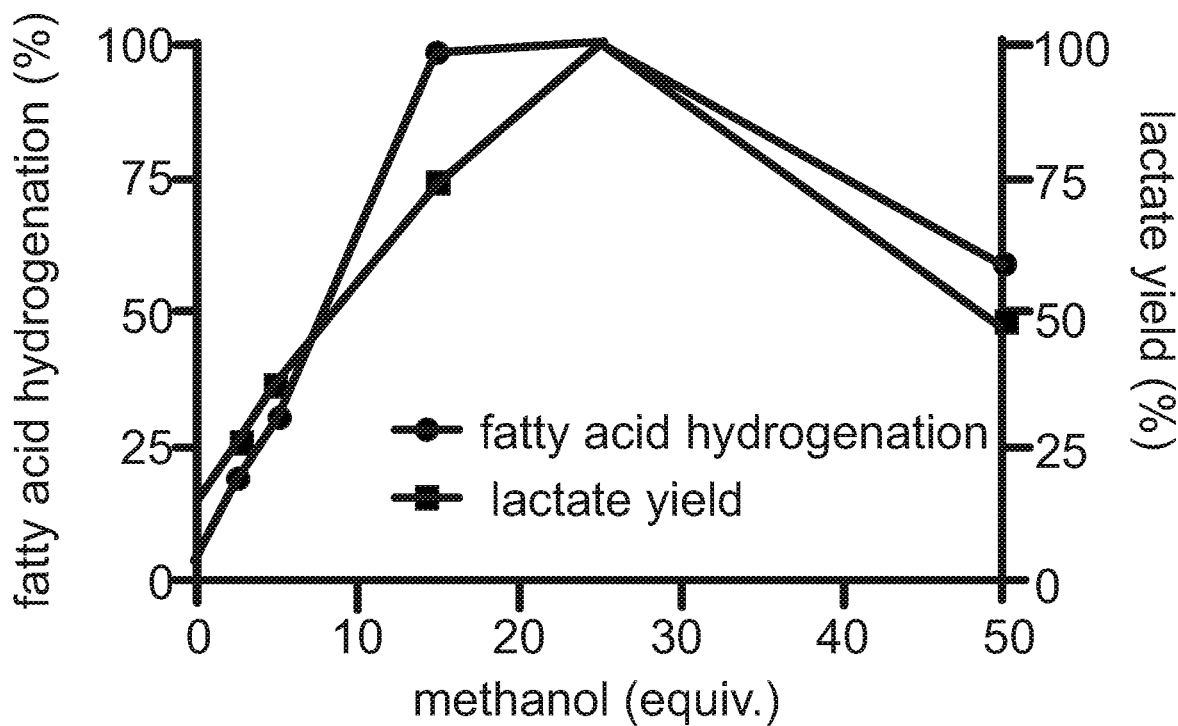
FIGS. 1A, 1B, 1C and 1D. Impact of methanol, glycerol, and NaOH concentration on reaction yield. Conditions: 0.5 mL corn oil, 0.3 mol % Ir catalyst, 120° C., 1 day. A. Variable methanol concentration, 5 eq. NaOH. B. Variable glycerol concentration, no MeOH, 1 eq. NaOH to glycerol (no less than 5 eq. to triglyceride). C. Variable NaOH loading, 15 eq. MeOH. D. Variable H2O loading, 15 eq. MeOH, 5 eq. NaOH.

Reference will now be made in detail to presently preferred compositions, embodiments and methods of the present invention, which constitute the best modes of practicing the invention presently known to the inventors. The Figures are not necessarily to scale. However, it is to be understood that the disclosed embodiments are merely exemplary of the invention that may be embodied in various and alternative forms. Therefore, specific details disclosed herein are not to be interpreted as limiting, but merely as a representative basis for any aspect of the invention and/or as a representative basis for teaching one skilled in the art to variously employ the present invention.

Except in the examples, or where otherwise expressly indicated, all numerical quantities in this description indicating amounts of material or conditions of reaction and/or use are to be understood as modified by the word "about" in describing the broadest scope of the invention. Practice within the numerical limits stated is generally preferred. Also, unless expressly stated to the contrary: all R groups (e.g. $R_i$ where i is an integer) include hydrogen (H), alkyl, lower alkyl, $C_{1-6}$ alkyl, $C_{6-10}$ aryl, or $C_{6-10}$ heteroaryl; all L groups (e.g. $L_i$ where i is an integer) are ligands, examples of which include anionic ligands, dianionic ligands, bidentate ligands (if two bonds indicated); single letters (e.g., "n" or "o") are integers such as 1, 2, 3, 4, or 5; percent, "parts of," and ratio values are by weight; the description of a group or class of materials as suitable or preferred for a given purpose in connection with the invention implies that mixtures of any two or more of the members of the group or class are equally suitable or preferred; description of constituents in chemical terms refers to the constituents at the time of addition to any combination specified in the description, and does not necessarily preclude chemical interactions among the constituents of a mixture once mixed; the first definition of an acronym or other abbreviation applies to all subsequent uses herein of the same abbreviation and applies mutatis mutandis to normal grammatical variations of the initially defined abbreviation; and, unless expressly stated to the contrary, measurement of a property is determined by the same technique as previously or later referenced for the same property.

It is also to be understood that this invention is not limited to the specific embodiments and methods described below, as specific components and/or conditions may, of course, vary. Furthermore, the terminology used herein is used only for the purpose of describing particular embodiments of the present invention and is not intended to be limiting in any way.

It must also be noted that, as used in the specification and the appended claims, the singular form "a," "an," and "the" comprise plural referents unless the context clearly indicates otherwise. For example, reference to a component in the singular is intended to comprise a plurality of components.

The term "comprising" is synonymous with "including," "having," "containing," or "characterized by." These terms are inclusive and open-ended and do not exclude additional, unrecited elements or method steps.

The phrase "consisting of" excludes any element, step, or ingredient not specified in the claim. When this phrase appears in a clause of the body of a claim, rather than immediately following the preamble, it limits only the element set forth in that clause; other elements are not excluded from the claim as a whole.

The phrase "consisting essentially of" limits the scope of a claim to the specified materials or steps, plus those that do not materially affect the basic and novel characteristic(s) of the claimed subject matter.

With respect to the terms "comprising," "consisting of," and "consisting essentially of," where one of these three terms is used herein, the presently disclosed and claimed subject matter can include the use of either of the other two terms.

The term "alkyl" refers to $C_{1-20}$ inclusive, linear (i.e., "straight-chain"), branched, saturated or at least partially and in some cases fully unsaturated (i.e., alkenyl and alkynyl) hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, and allenyl groups. "Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms.

In a variation, the term "aryl" means an aromatic radical such as a phenyl group, a naphthyl group, a biphenyl group, a phenyl group substituted by 1 to 4 substituents selected from alkyl as defined above, alkoxy as defined above, thioalkoxy as defined above, hydroxy, halogen, trifluoromethyl, amino, alkylamino as defined above for alkyl, dialkylamino as defined for alkyl, N-acetylamino, cyano —$SO_2NH_2$, or nitro, a naphthyl group substituted by 1 to 4 substituents as defined above for a phenyl group substituted by 1 to 4 substituents, or a biphenyl group substituted by 1 to 4 substituents as defined above for a phenyl group substituted by 1 to 4 substituents. In a refinement, aryl is a $C_{6-18}$ aryl.

In a variation, the term "heteroaryl" means a $C_{5-13}$ heteroaromatic radical such as 2- or 3-thienyl; 2- or 3-furanyl; 1-, 2- or 3-pyrrolyl; 1-, 2-, 4-, or 5-imidazolyl; 1-, 3-, 4-, or 5-pyrazolyl; 2-, 4-, or 5-thiazolyl; 3-, 4-, or 5-isothiazolyl; 2-, 4-, or 5-oxazolyl; 3-, 4-, or 5-isoxazolyl; 1-, 3-, or 5-1,2,4-triazolyl; 1-, 2-, 4-, or 5-1,2,3-triazolyl; 1- or 5-tetrazolyl; 4-, or 5-1,2,3-oxadiazolyl; 3-, or 5-1,2,4-oxadiazolyl; 2-1,3,4-oxadiazolyl; 2-1,3,4-thiadiazoyl; 2-1,3,5-triazinyl; 3-pyridinyl; 3-, 4-, or 5-pyridazinyl; 2-pyrazinyl; 2-, 4-, or 5-pyrimidinyl; unsubstituted or substituted by 1 to 2 substituents selected from $NH_2$, OH, S, halogen as defined hereinafter, alkyl as defined above, or alkoxy as defined above. In a refinement, heteroaryl is a $C_{5-18}$ heteroaryl.

In a variation, the term "halogen" or "halo" means fluorine, chlorine, bromine, or iodine.

In a variation, a "linking ligand" is a ligand that attached two chemical moieties together.

It should be appreciated that all cationic species are charged balanced by an appropriate number of negatively charged counterions $X^-$ (e.g., trifluoromethanesulfonate, halide, sulfate, phosphate, and the like.)

It should be appreciated that each C—H bond in the formulae set forth herein can be substituted. For example, each C—H bond can be substituted by halo, cyano, nitro, hydroxyl, $C_{1-10}$ alkyl, $C_{1-8}$ alkoxyl, $C_{6-14}$ aryl, $C_{5-3}$ heteroaryl, $NH_2SO_2R$, $CF_3$, arylsulfonyl, arylsulfonamide, o-$OCH_3$, pyridinyl, bipyridinyl, phenyl, chloro, bromo, fluoro, and the like. Such substituted C—H bonds can be symbolized by C—$R^z$ where z is an integer from 1 to 100 that has not already been used as a subscript or subscript for an R group.

It should also be appreciated that integer ranges explicitly include all intervening integers. For example, the integer range 1-10 explicitly includes 1, 2, 3, 4, 5, 6, 7, 8, 9, and 10. Similarly, the range 1 to 100 includes 1, 2, 3, 4 . . . 97, 98, 99, 100.

Throughout this application, where publications are referenced, the disclosures of these publications in their entireties are hereby incorporated by reference into this application to more fully describe the state of the art to which this invention pertains.

Abbreviations

"mes" is mesityl;

"OTf" is trifluoromethanesulfonate.

"Macho" means $R_2CH_2CH_2NHCH_2CH_2PR_2$ where R is $C_{1-6}$ alkyl, a particularly useful example $P(CH_2)_2NH(CH_2)_2P$.

In general, a method in which hydrogen is transferred from glycerol to unsaturation in the lipids from which a biodiesel can be produced is provided. In particular, the methods are directed to the two most popular U.S. feedstocks, soybean and corn oils.[6] Other oils such as red palm and coconut oils are also examined. These have limited applicability to our method, because of their low unsaturation levels, although they are suitable substrates in our hands. Table 1 shows the major fatty acid components in soybean oil and corn oil as measured in our lab by NMR. Both oils are extensively unsaturated, which lowers their biodiesel value: polyunsaturation in diesel fuels causes inferior stability, engine lubrication failure, slow ignition, and high emission of hydrocarbons and particulates.[7] While these unsaturated oils can be hydrogenated over heterogeneous catalysts (e.g. Pd),[8] this involves cost and safety issues associated with high pressure hydrogenation.

TABLE 1

Fatty Acid Composition of Natural Oils[a]

|  | Palmitic (16:0) | Stearic (18:0) | Oleic (18:1) | Linoleic (18:2) | Linolenic (18:3) |
| --- | --- | --- | --- | --- | --- |
| Soybean | 11.9% | 4.2% | 22.6% | 53.5% | 6.1% |
| Corn | 6.5% | 1.4% | 39.9% | 50.1% | 0.6% |

[a]Determined in triplicate by $^1$H-NMR.

In an embodiment, a method extracting embedded hydrogen from glycerol or a compound containing functionalized glycerol is provided. The method includes a step of combining a glycerol-containing compound with a transition metal catalyst system to form a first composition. In a variation, the first composition includes a base. Characteristically, the transition metal catalyst system includes a first organometallic complex having a transition metal M. In one variation, hydrogen gas (i.e., $H_2$) is extracted from (e.g. created from) the first composition. In another variation, hydrogen is transferred to an unsaturated hydrogen receptor that includes an unsaturated moiety (e.g., C=C or C=O) to form a second composition. In a refinement, the glycerol-containing compound is free glycerol or a glyceride ester. Particularly useful glycerol-containing compounds includes vegetable oils such as corn oil, soy oil, and other vegetable oils having fatty acid group with a least one degree of unsaturation. Typically, these reactions steps are performed at a reaction temperature from about 100 to 290° C.

Although the present embodiment is not limited by the concentrations of the reactants, typically the concentration of the glycerol-containing compound is from about 1 to about 100 weight percent of the total weight of the first composition. In refinement, the concentration of the glycerol-containing compound is at least, in increasing order of preference, 1, 2, 5, 10, 20, 30, 40 or 50 weight percent of the total weight of the first composition and at most, in increasing order of preference, 100, 99, 98, 95, 90, 80, 70, or 60 weight percent of the total weight of the first composition. Similarly, the concentration of the unsaturated hydrogen receptor is from about 1 to a about 100 weight percent of the total weight of the first composition. In refinement, the concentration of the unsaturated hydrogen receptor is at least, in increasing order of preference, 0, 0.1, 1, 2, 5, 10, 20, 30, 40 or 50 weight percent of the total weight of the first composition and at most, in increasing order of preference, 100, 99, 98, 95, 90, 80, 70, or 60 weight percent of the total weight of the first composition. When present, the concentration of the base is from about 1 to a about 100 weight percent of the total weight of the first composition. In refinement, the concentration of base is at least, in increasing order of preference, 0, 0.1, 1, 2, 5, 10, 20, 30, 40 or 50 weight percent of the total weight of the first composition and at most, in increasing order of preference, 100, 99, 98, 95, 90, 80, 70, or 60 weight percent of the total weight of the first composition.

In some refinements, a $C_{2-3}$ carboxylate is formed by reaction of the glycerol-containing compound with the transition metal catalyst system. For example, a lactate or acetate can be formed by reaction of the glycerol-containing compound with the transition metal catalyst system.

In a refinement, a salt is formed by the method set forth above. Advantageously, such a salt can be dissolved in an aqueous solution and the salt is crystallized from this solution. In a further refinement, the salt is purified by passing through a resin.

In a particularly useful variation, the glycerol-containing compound (e.g., a triglyceride) includes at least one unsaturated fatty acid group that has at least one degree of unsaturation such that the first composition includes a reactant fatty acid or reactant fatty acid salt resulting in the second composition including an ester of a fatty acid having a lower degree of unsaturation than the unsaturated fatty acid group in the glycerol-containing compound wherein hydrogen for reduction comes from the glycerol formed from the glycerol-containing compound. Advantageously, free fatty acids or the fatty acid esters are isolated by aqueous extraction to remove impurities and afford pure fatty acid or fatty acid esters.

In another variation, the transition metal catalyst system further includes an iron-containing complex, the iron-containing complex being different than the first organometallic complex.

In another variation, an acid is combined with the glycerol-containing compound and a first transition metal catalyst to form the second composition.

In still another variation, the second composition further includes an alcohol, and in particular, a $C_{1-5}$ alcohol such as methanol and ethanol.

In still another variation, the first composition and/or the second composition further includes a lactide or polylactide.

In another embodiment, a method for converting triglycerides to a biodiesel fuel and poly(lactic acid) is provided. The method includes a step of combining a triglyceride (e.g., a vegetable oil) with a transition metal catalyst system to form a first composition that includes a reactant fatty acid and/or reactant fatty acid salt and a lactide and/or polylactide. The first transition metal catalyst system includes a first organometallic complex having a transition metal M. In a refinement, a base (e.g., NaOH, KOH or $Ca(OH)_2$) is also combined with the triglyceride and the transition metal catalyst system. In one variation, the transition metal catalyst system includes an iridium containing catalyst. Characteristically, the triglyceride includes an unsaturated fatty acid group that has at least one degree of unsaturation. The first composition is combined with an alcohol (e.g., $C_{1-6}$ alcohol) to form a second composition that includes an ester of a fatty acid having a lower degree of unsaturation than the unsaturated fatty acid group in the triglyceride. In other words, the unsaturated fatty acid group in the triglyceride has been reduced. Characteristically, the hydrogen for the reduction comes from glycerol component of the triglyceride and/or glycerol formed from the triglyceride. In another refinement, an acid is combined with the first composition and alcohol in forming the second composition in order to promote ester formation.

Figure 3:
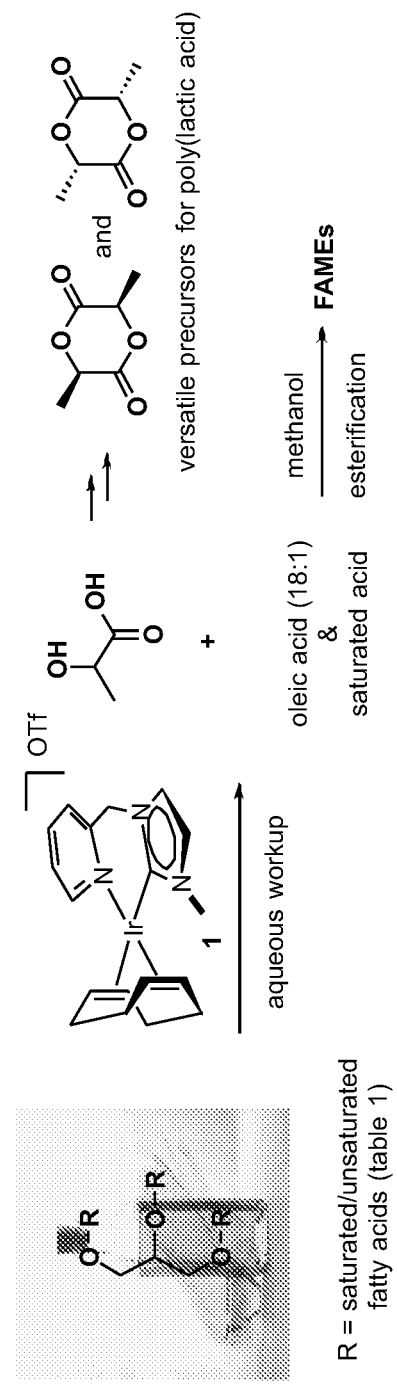
FIG. 3. Scheme 2 showing iridium catalysis enabling vegetable oil conversion to FAMEs and Lactate.

Examples of useful catalysts that can be used in the methods contained herein are set forth in U.S. Pat. Pub. No. 2017/0217870 and 2017/0014817; the entire disclosures of which are hereby incorporated by reference. Various catalytic dehydrogenation methods have been developed.[5,9] In particular, conditions have been reported for converting crude glycerol from biodiesel waste streams to lactide, a precursor for poly(lactic acid), with turnover numbers exceeding 4 million.[5] Moreover, this catalyst has been shown to dehydrogenate several alcohols, including methanol. Together, these tools enable a tandem approach for the synthesis of FAMEs with no glycerol waste stream. This is exemplified in Scheme 2 (FIG. 3), where corn oil is converted smoothly to hydrogenated biodiesel and lactic acid.

In a variation, the transition metal catalyst system further includes an iron containing complex where the iron-containing complex is different than the first organometallic complex. An example of such an iron-containing complex is (Macho)Fe.

In variation, the transition metal catalyst system used in the methods herein includes an organometallic complex having formula I which advantageously has a sterically protecting NHC carbene-pyridine ligand to handle harsher reaction conditions than many prior art catalysts:

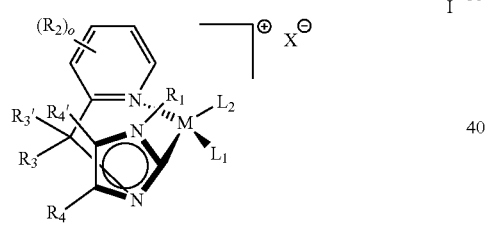

wherein:
M is a transition metal;
o is 0, 1, 2, 3, or 4;
$R_1$ is a $C_{1-6}$ alkyl, a $C_{6-18}$ aryl, or an optionally substituted $C_{5-18}$ heteroaryl. In a refinement, $R_1$ is mesityl, methyl, ethyl, butyl, n-propyl, isopropyl, n-butyl, sec-butyl, or t-butyl; $R_2$ are independently an optionally substituted $C_{1-6}$ alkyl, halo (e.g., Cl, F, Br, etc.), $NO_2$, an optionally substituted $C_{6-18}$ aryl, or an optionally substituted $C_{5-18}$ heteroaryl;
$R_3$, $R_3'$ are independently hydrogen, an optionally substituted $C_{1-6}$ alkyl, halo (e.g., Cl, F, Br, etc.), $NO_2$, an optionally substituted $C_{6-18}$ aryl, or an optionally substituted $C_{5-18}$ heteroaryl;
$R_4$, $R_4'$ are independently hydrogen, an optionally substituted $C_{1-6}$ alkyl, halo (e.g., Cl, F, Br, etc.), $NO_2$, an optionally substituted $C_{6-18}$ aryl, or an optionally substituted $C_{5-18}$ heteroaryl, or an annulated aromatic ring (i.e., $R_4$ and $R_4'$ are bonded together to form a 5 or 6 member aromatic ring fused to the NHC carbine ring);
$X^-$ is a negatively charge counter ion such as halide or trifluoromethanesulfonate (OTf); and $L_1$, $L_2$ are each independently a neutral ligand or a charged ligand (e.g., positive or negative). Examples of such neutral ligands include, but are not limited to, carbon monoxide, triphenylphosphine, $CH_3CN$ $C_5H_5N$, $H_2O$, $NH_3$, arene, and combinations thereof, and the like. Examples of charge ligands include, but are not limited to, oxide, hydride, hydroxide, and alkoxide. In a refinement, $L_1$ and $L_2$ are combined together to form a neutral bidentate ligand as illustrated in the following formula II:

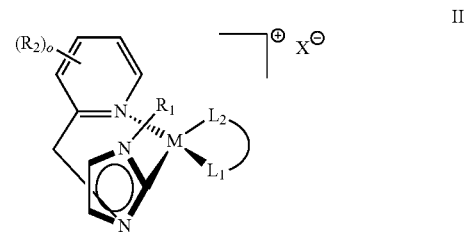

These bidentate ligands can be $C_{5-10}$ bis(alkene) ligands, $C_{5-10}$ bis(alkyne) ligands, $C_{2-10}$ diamine ligands, $C_{2-10}$ diphosphine ligands, $C_{2-10}$ bis(nitrile) ligands, $C_{2-10}$ bis(isonitrile) ligands, and the like. Examples of useful bidentate ligands include, but are not limited to, norbornadiene, 1,5-cyclooctadiene, ethylenediamine, 2,2'-bipyridine, and the like.

In a variation, the first organometallic complex is described by formula III:

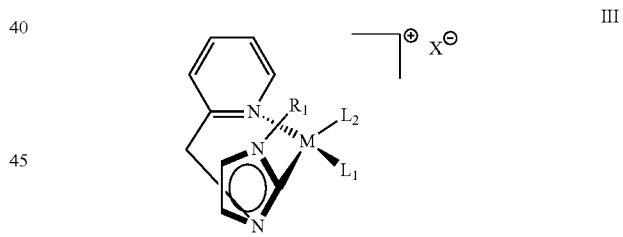

where $R_1$, $L_1$, $L_2$, $X^-$, and M are as set forth herein. Particularly useful organometallic complexes are described by formulas IV and V:

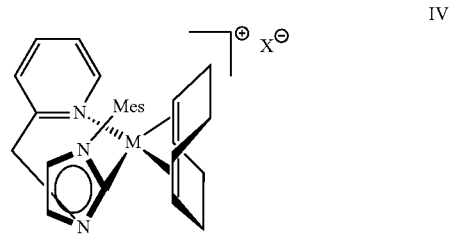

-continued

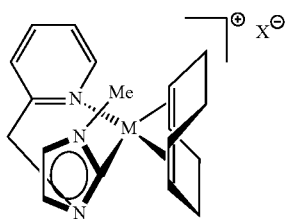
(V)

where M and X⁻ are as set forth herein.

In a refinement, the catalyst system also includes a base as a co-catalyst. In a refinement, the ligands in formulae I-V are optionally substituted with one or more groups at any position with $C_{1-6}$ alkyl, halo, nitro and the like. In another refinement, the ligands in formula I are optionally substituted with one or more groups at any position with methyl, ethyl, butyl, n-propyl, isopropyl, n-butyl, sec-butyl, and/or t-butyl.

In still another variation, the first organometallic complex has formula VI:

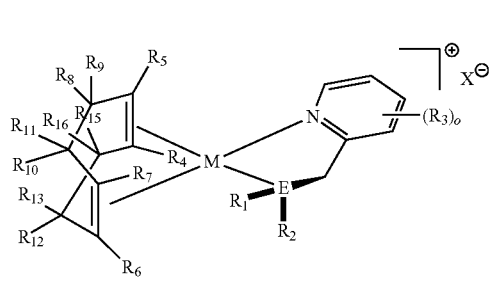
(VI)

wherein:

M is a transition metal; E is P, N, or C (as in imidazolium carbene);

$R_1$, $R_2$ are each independently $C_{1-6}$ alkyl groups;

$R_3$ are each independently hydrogen, $C_{1-6}$ alkyl groups, $OR_{14}$, $NO_2$, or halogen;

o is 1, 2, 3, or 4;

$R_4$, $R_5$, $R_6$, $R_7$, $R_8$, $R_9$, $R_{10}$, $R_{11}$, $R_{12}$, $R_{13}$, $R_{15}$, $R_{16}$ are each independently hydrogen or $C_{1-6}$ alkyl groups;

$R_{14}$ is hydrogen or $C_{1-6}$ alkyl group; and

X⁻ is a negatively charge counter ion such as halide or trifluoromethanesulfonate (OTf). Typically, the catalyst system also includes a base as a co-catalyst.

Typically, the catalyst system also includes a base as a co-catalyst. In another variation, $R_1$, $R_2$ are methyl, ethyl, butyl, n-propyl, isopropyl, n-butyl, sec-butyl, t-butyl. In a refinement, $R_1$, $R_2$ are t-butyl. In still another variation, the $R_3$ are each independently selected from the group consisting of hydrogen, methyl, ethyl, butyl, n-propyl, isopropyl, n-butyl, sec-butyl, t-butyl. In a refinement, the $R_3$ are hydrogen. In yet another variation, $R_4$, $R_5$, $R_6$, $R_7$, $R_8$, $R_9$, $R_{10}$, $R_{11}$, $R_{12}$, $R_{13}$, are each independently methyl, ethyl, butyl, n-propyl, isopropyl, n-butyl, sec-butyl, t-butyl. In a refinement, the $R_4$, $R_5$, $R_6$, $R_7$, $R_8$, $R_9$, $R_{10}$, $R_{11}$, $R_{12}$, $R_{13}$ are each independently hydrogen. In a refinement, the first organometallic complex is described by formula VII:

In still another variation, the first organometallic complex has formula VII:

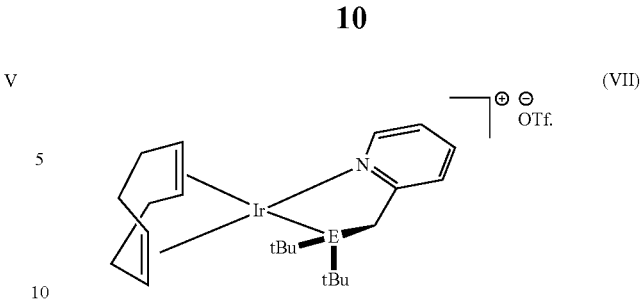
(VII)

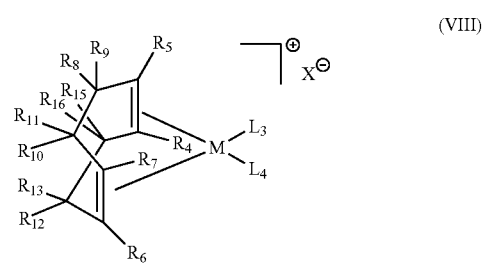
(VIII)

wherein:

M is a transition metal;

$R_4$, $R_5$, $R_6$, $R_7$, $R_8$, $R_9$, $R_{10}$, $R_{11}$, $R_{12}$, $R_{13}$, $R_{15}$, $R_{16}$ are each independently hydrogen or $C_{1-6}$ alkyl groups as set forth above;

X⁻ is a negatively charged counter ion such as halide or trifluoromethanesulfonate (OTf); and $L_3$, $L_4$ are each independently a neutral ligand or a charged ligand (e.g., positive or negative). Examples of such ligands include, but are not limited to, carbon monoxide, triphenylphosphine, $CH_3CN$ $C_5H_5N$, $H_2O$, $NH_3$, arene, and combinations thereof, and the like.

In still another variation, the first organometallic complex has formula IX:

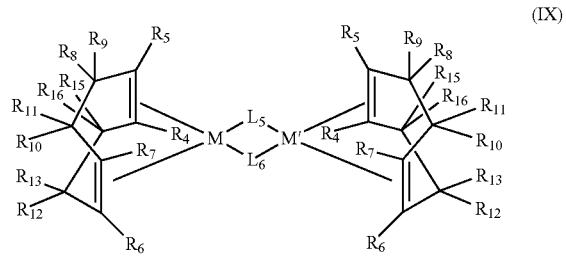
(IX)

wherein:

M, M' are each independently a transition metal where M and M' can be the same or different;

$R_4$, $R_5$, $R_6$, $R_7$, $R_8$, $R_9$, $R_{10}$, $R_{11}$, $R_{12}$, $R_{13}$, $R_{15}$, $R_{16}$ are each independently hydrogen or $C_{1-6}$ alkyl groups as set forth above; and $L_5$, $L_6$ are each independently a bidentate ligand, a linking ligand (e.g., a dianionic linking ligand), a neutral ligand, or an monoanionic ligand (e.g., halide such as Cl, Br, I, etc.). If the compound of formula (IX) has a positive charge (e.g., 1+, 2+, 3+ etc.) there will be a sufficient number of counter ions X⁻ as set forth above to maintain charge neutrality.

In the embodiments, variations and refinements set forth above, M and M' are each independently a metal selected from the group consisting of beryllium, magnesium, aluminum, scandium, titanium, vanadium, chromium, manganese, iron, cobalt, nickel, copper, zinc, gallium, germanium, yttrium, zirconium, niobium, molybdenum, technetium, ruthenium, rhodium, palladium, silver, cadmium, indium, tin, antimony, lanthanum, cerium, praseodymium, neodymium, promethium, samarium, europium, gadolimium, terbium, dysprosium, holmium, erbium, thalium, ytterbium, lutetium, hafnium, tantalum, tungsten, rhenium, osmium, iridium, gold, platinum, thallium, lead, bismuth, polonium, thorium, protactinium, uranium, neptunium, and plutonium. In a refinement, M and M' are each independently a transition metal selected from the group consisting of ruthenium, rhodium, iridium, and iron. In another refinement, M and M' are each independently iridium.

In a refinement, the catalyst systems set forth above can also include a base as a co-catalyst. In a refinement, the ligands in formula I—IX are optionally substituted with $C_{1-6}$ alkyl, halo, nitro and the like at any position. In another refinement, the ligands in formula I-IX can optionally be substituted with methyl, ethyl, butyl, n-propyl, isopropyl, n-butyl, sec-butyl, and/or t-butyl at any position.

The following examples illustrate the various embodiments of the present invention. Those skilled in the art will recognize many variations that are within the spirit of the present invention and scope of the claims.

To test the tandem reaction, neat corn oil and complex 1 were combined in a sealed vessel with NaOH, and the solution was heated (Table 2). Hydrogen pressure evolved, and double bonds of the fatty acids were reduced. Only polyunsaturated fatty acids were reduced under our iridium conditions. The selectivity is striking. In both corn and soybean oils, polyunsaturated acids can be completely hydrogenated to oleic acid (18:1). Simultaneously, oleic acid (18:1) stays intact. The degree of hydrogenation reported in Table 2 therefore describes the portion of polyunsaturated acids that are reduced (to oleate). The stability of oleic acid through the reduction is significant, because methyl oleate provides important low temperature fluidity in the biodiesel FAME blend produced in these reactions. In our case, the product is FAMEs with 84-92% oleate content, which provide necessary resistance to precipitate formation in the engine, in contrast to the troublesome precipitation of FAMEs of fully saturated fatty acids (e.g. 16:0 and 18:0).

In a first-pass experiment (Table 2, entry 1), both lactate (15%) and fatty acid hydrogenation were observed. The glyceride fragment of corn oil did not provide enough reducing equivalents to reduce all of the fatty acids, so only 5% of olefins were reduced. The reaction mixture turns into a biphasic soapy mass in just a few hours, which prevents efficient mixing of the catalyst with unsaturated fatty acids. We addressed both problems with the addition of either methanol (entry 2) or glycerol (entry 3). Each worked well, enabling complete hydrogenation and improved lactate yields. Taking advantage of the high conversion and selectivity available with added methanol, we were able to esterify crude fatty acid with methanol to yield desired FAMEs with an overall isolated yield of 65%. Lactate is also isolated and converted to lactide using methods similar to those previously reported.[5] In reactions with glycerol as the reducing agent, a longer reaction time enables a higher yield of lactate: compare entries 3 and 4 in which yield increases from 48% to 76% as time is extended from 3 to 7 days. These observations are not limited to corn oil; we observe comparable results for soybean oil (entry 5). Catalyst 1 also has good longevity. Using only 30 ppm of 1 provides satisfying results, delivering over 230,000 turnovers (entry 6).

While we found C—N-ligated complex 1 to be the best catalyst precursor for glycerol to lactate conversion[5] and it performed well in this tandem process, we examined a number of related iridium(I) precursors for comparative and control purposes. These are sketched in Table 2. Complex 2 is a bulkier, C—N-ligated version of 1 prepared in an analogous way. Complex 3 is a P—N homolog of 1 that works well in our hands in dehydrogenation of formic acid and alcohols.[9b] 4 is Crabtree's catalyst, presented here as an acyclic homolog of 3, and 5 is the iridium precursor from which our chelates are prepared.

TABLE 2

Catalytic Hydrogenation of Polyunsaturation in Corn and Soybean Oils[a]

| Entry | Catalyst | Reductant (equiv.) | | Degree of hydrogenation | Lactate yield (equiv.)[b] |
|---|---|---|---|---|---|
| | | MeOH | Glycerol | | |
| 1 | 1 | 0 | 0 | 5% | 0.15 |
| 2 | 1 | 25 | 0 | 100% (65%)[g] | 1.00[h] |
| 3[c] | 1 | 0 | 25 | 99% | 12.1 |
| 4[d] | 1 | 0 | 25 | 90% | 19.0 |
| 5[e] | 1 | 25 | 0 | 98% | 0.70 |
| 6[c,f] | 1 | 25 | 0 | 91% | 0.72 |
| 7 | 2 | 25 | 0 | 82% | 0.58 |
| 8 | 3 | 25 | 0 | 98% | 0.75 |
| 9 | 4 | 25 | 0 | 74% | 0.51 |
| 10 | 5 | 25 | 0 | 59% | 0.17 |

[a]Reaction condition: 0.5 mL corn oil, 0.3 mol % Ir complex, 5 eq. NaOH, 120° C., 1 day. Degree of hydrogenation refers only to linolenic acids and excludes oleic acid.
[b]Determined by $^1$H-NMR.
[c]Reaction time was 3 days with 10 eq. NaOH.
[d]Reaction time was 7 days with 25 eq. NaOH.
[e]Soybean oil was used in place of corn oil.
[f]Catalyst loading was 30 ppm, total TON > 230k.
[g]Isolated yield of FAMEs after esterification with methanol.
[h]>99% NMR conversion of glyceride to lactate.

Generally, iridium complexes 2-5 are marginally less effective than 1 in the tandem reaction. Under the same reaction conditions, less fatty acid was hydrogenated or less lactate was produced in each case (Table 2, entry 7-10). Owing to its bulky mesityl group, 2 reacts more slowly than 1 (entry 7). The P—N complex 3 showed the closest reactivity to 1 (entry 8), although its acyclic congener (4) is less efficient (entry 9). This shows that the supporting C—N or P—N ligand on the iridium plays an important role in the reactivity. Along these lines, iridium precursor 5 proved to be poor in both hydrogenation and dehydrogenation (Table 2, entry 10).

Figure 1B:
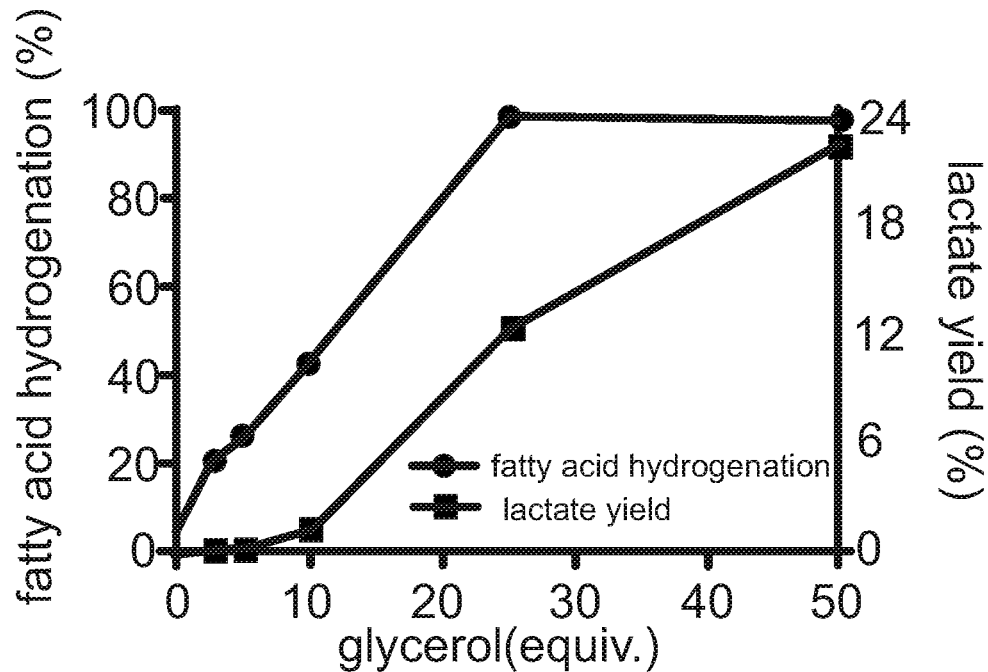

In any given implementation of our tandem synthesis, practitioners might choose to tune product distribution to a certain product need or feedstock availability. To aid in this, we have measured the following reaction performance parameters. In varying the methanol loading from 0 to 50 equivalents relative to corn oil, we observed near quantitative hydrogenation of fatty acid and near perfect glyceride to lactate conversion when 15 to 25 equivalents methanol are used (FIG. 1A). In each case, formate appears as the side product. Hence, we believe methanol is an outstanding reductant/solvent for this reaction at an optimal concentration. Further increasing methanol concentration beyond 25 equivalents resulted in lower conversion. This appears to result from catalyst deactivation in presence of high concentrations of methanol. We observe the same in a previous study that shows that although iridium 1 is an active methanol dehydrogenation catalyst and a robust catalyst for glycerol dehydrogenation, in concentrated aqueous methanol solution the catalyst is deactivated after only a few hundred turnovers. Similarly, when 1 is treated with a high methanol loading in our tandem reaction, a fast catalyst speciation is observed by $^1$H-NMR.[5] In contrast, when varying the concentration of glycerol in our tandem system, a linear correlation is observed between yield and glycerol loading. Catalyst 1 produces more lactate from the added glycerol, but a longer reaction time is needed (FIG. 1B). This reactivity is consistent with 1's reaction with glycerol in the absence of fatty acids.

Figure 1C:
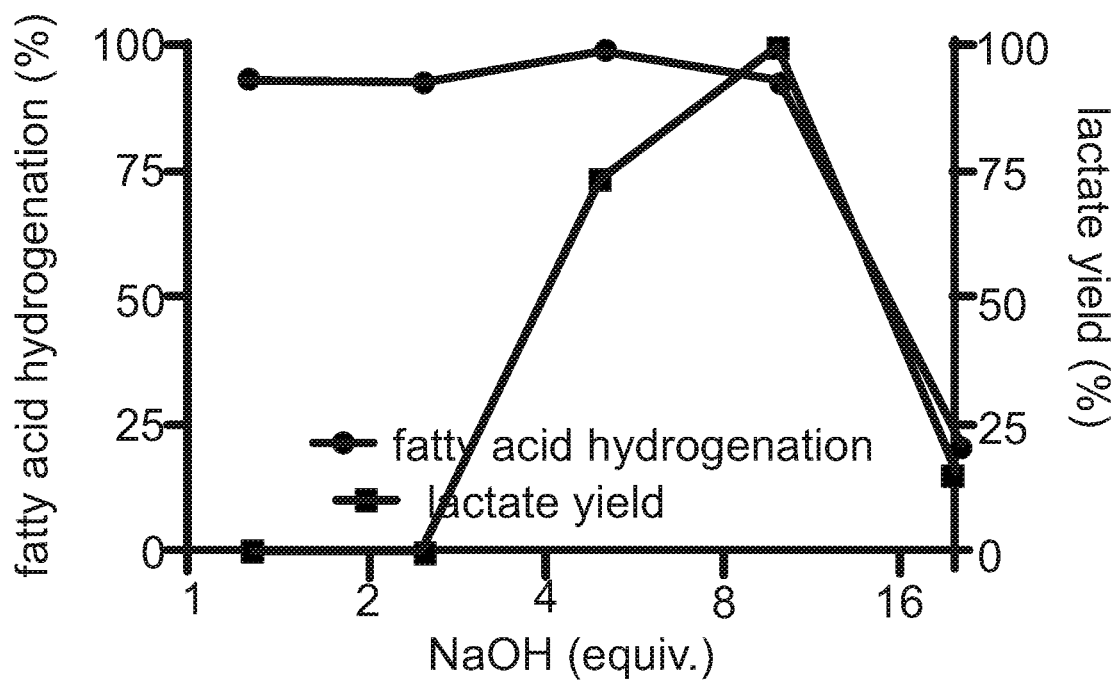
Figure 1D:
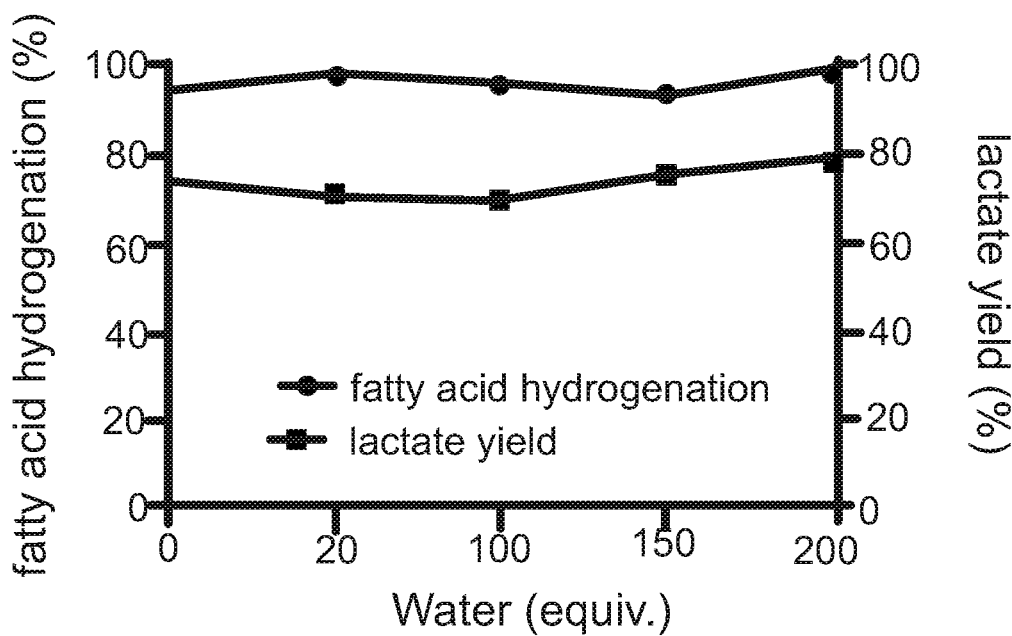
Figure 2:
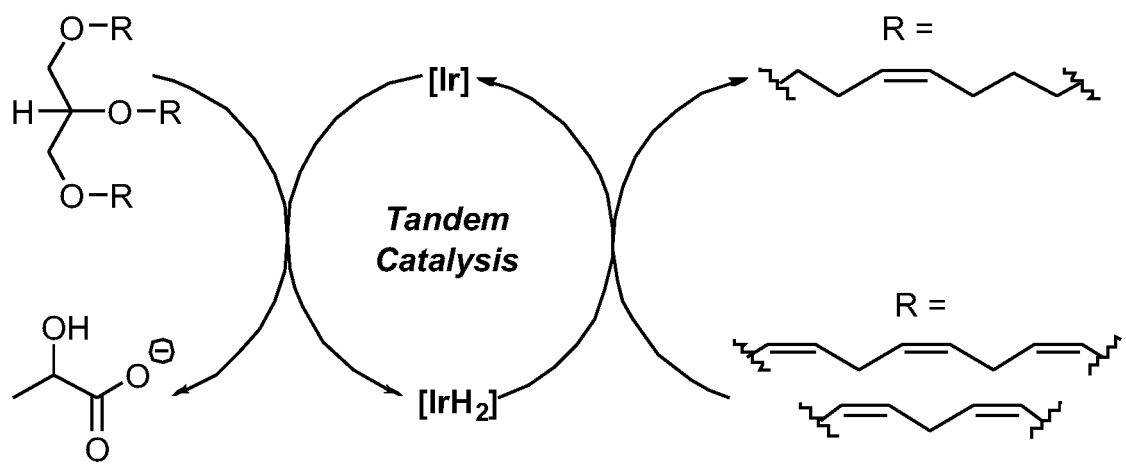
FIG. 2. Scheme 1 showing a general scheme for triglyceride utilization

A base loading study showed no conversion of glycerol up to 2.5 equivalents of NaOH, although >90% hydrogenation of the fatty acids was observed (FIG. 1C). This means that stoichiometric base is not required for olefin hydrogenation. This observation implies that fast, base-free transfer hydrogenation from methanol to fatty acid is responsible for the fatty acid hydrogenation and that glycerol is not derivatized in this process. Such a transfer hydrogenation path can also explain the reactivity observed for iridium complexes 2, 3, 4, and 5 in which a relatively high degree of hydrogenation is observed with a relatively low level of glycerol conversion. The system also shows useful water resistance (FIG. 1D). With up to 200 equiv. additional $H_2O$, we observed no change in catalytic reactivity.

While we do observe the evolution of hydrogen pressure in our tandem reaction, it is not obvious whether $H_2$ release from the catalyst is necessary, deleterious, or simply a side reaction. Thus, we want to know whether $H_2$ gas can be re-activated by our catalyst once formed, or whether we have a more traditional hydrogen borrowing mechanism,[10] wherein proton and hydride must remain bound to the catalyst in order to be transferred to olefins. While some iridium catalysts supported by C—N chelates are known to hydrogenate olefins at room temperature and low pressure conditions,[11] we have not previously observed the same with 1. Thus, a model reaction was set up in which a 1,2-dichloroethane solution of corn oil and 1 (0.3 mol %) was charged with 1.0 atmosphere of $H_2$. After the reaction was stirred at 60° C. for 2 days, a modest portion (9%) of hydrogenation was observed. This shows that $H_2$ activation with our catalyst is possible, but olefin hydrogenation from $H_2$ is too slow to account for the performance of the tandem reaction. In a complementary experiment, we ran the reaction in a flask such that $H_2$ gas was vented to a eudiometer. Here we observe 25% hydrogenation of olefins. This evidence supports a base-free hydrogen borrowing mechanism for a considerable portion of the olefin conversion.

Figure 4A:
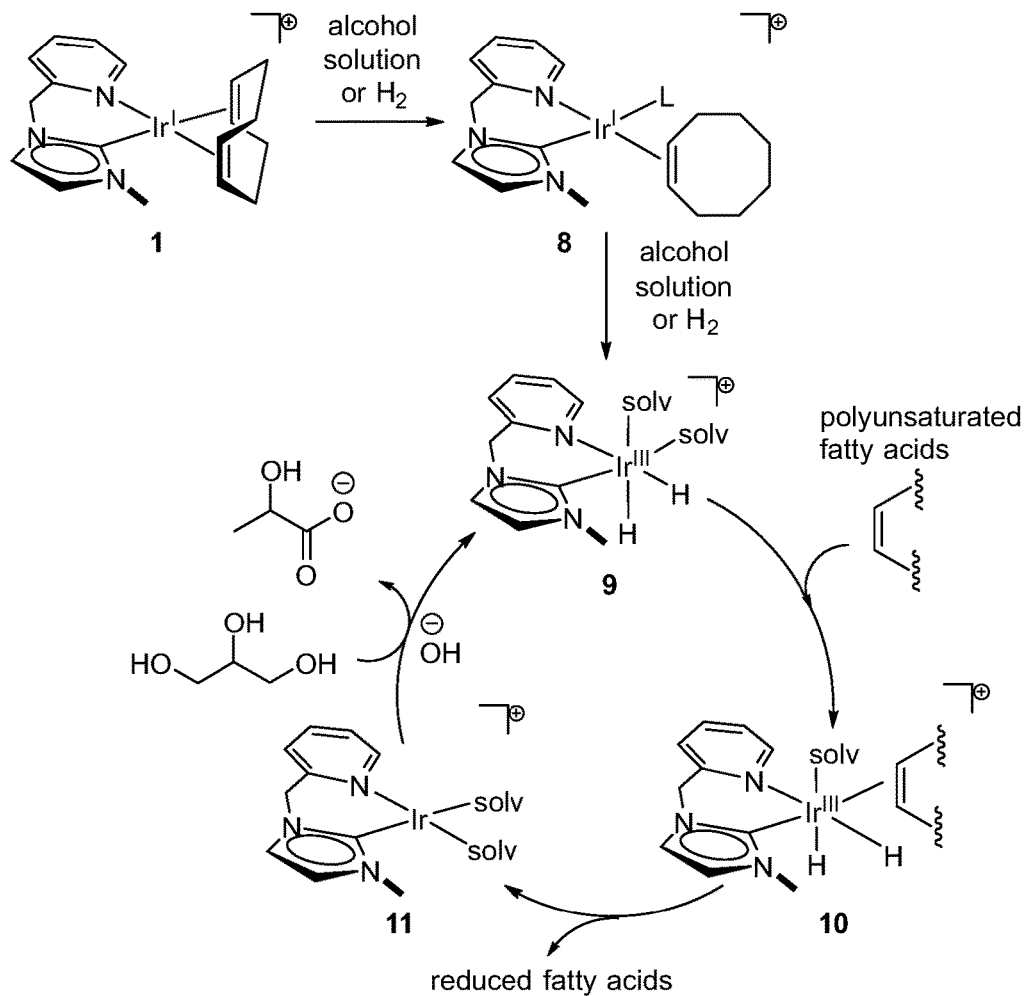
FIGS. 4A and 4B. A) Scheme 3 showing Transfer hydrogenation by hydrogen borrowing and B) an ORTEP Diagram of Complex 6.
Figure 4B:
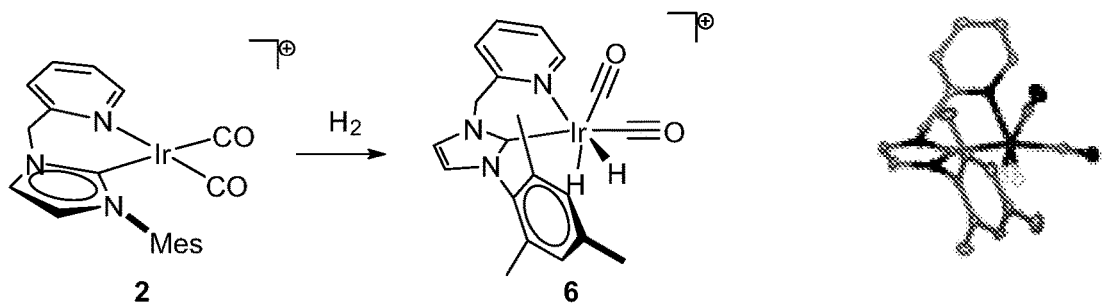

Finding hydrogen borrowing is curious to us, because our group was never able to observe a long-lived hydride of 1 or any of its (C—N)IrLn congeners while we have characterized several hydrides that derive from P—N-supported iridium precursor 3.[9b] For a base-independent hydrogen borrowing situation, we must have a long-lived iridium hydride intermediate in our mechanism. This iridium hydride species is most likely monomeric, according to kinetic data we reported for alcohol dehydrogenation by 1.[5] We assumed that a hydride of 1 would be too high in energy for observation under catalytic conditions. We therefore went about the isolation of a (C—N)Ir—H species from carbonyl ligated iridium 2 with the expectation that carbonyl groups would stabilize a hydride species. Treatment of 2 with a pressure of $H_2$ allowed for clean conversion to and crystallization of dihydride 6. Based on the structure of 6 and observations mentioned above, we propose a general pathway illustrated in Scheme 3 (FIG. 4). In this mechanism, 1 is initiated by hydrogenation and loss of its cyclooctadiene ligand via 8, which is observable on the NMR time scale, to an active species such as 9. We expect 9 to hydrogenate alkenes without the aid of base to give 11. Intermediate 11 can dehydrogenate glycerol in the presence of hydroxide. We expect the details of these steps to conform to traditional iridium-based olefin hydrogenation mechanisms.[12]

While unreduced methyl oleate has value in biodiesel blends, we wanted to identify conditions for complete reduction of all unsaturation in a sample of vegetable oil. Starting from our original conditions, increasing the loading of 1 to 6 mol %, and raising the reaction temperature to 150° C., we observed over 95% hydrogenation of unsaturated fatty acids (Table 3, entry 1). We perceive that our intermediate iridium hydride species is prone to decomposition and deactivation, and that this is why excess reducing equivalents limit its lifetime. To obviate this problem (and mitigate the cost of iridium), we show that the addition of a second catalyst can enable total reduction without requiring high [Ir] loading. We find iron complex 7 to be quite useful in this role (entries 3-5). By adding 7 along with 1, up to 90% of total hydrogenation could be achieved.

TABLE 3

Full Hydrogenation of Corn Oil Fatty Acids[a]

| Entry | Ir catalyst | Fe catalyst | full hydrogenation |
|---|---|---|---|
| 1 | 1 (6 mol %) | NA | 91% |
| 2 | 1 (0.3 mol %) | NA | 54% |
| 3 | 1 (0.3 mol %) | 7 (0.3 mol %) | 54% |
| 4 | 1 (0.3 mol %) | 7 (0.6 mol %) | 67% |
| 5 | 1 (0.3 mol %) | 7 (3.0 mol %) | 96% |

Reaction condition: 0.5 mL corn oil, 5 eq. NaOH, 120° C., 1 day, 25 eq. MeOH. Fatty acid hydrogenation was evaluated by $^1$H-NMR.

In conclusion, a high-utility process for the conversion of corn and soybean oils to value-added hydrogenated FAMEs and lactate is presented. The key step is a tandem fatty acid hydrogenation and glyceride dehydrogenation that is enabled by a (carbene)iridium complex. The system has useful longevity and yield and is highly selective for the hydrogenation of polyunsaturated fatty acids. It is also shown that an iridium-iron catalysis cascade can almost completely hydrogenate the fatty acids. Experimental data support a mechanism involving hydrogen borrowing. The hydrogen carrier appears to be a mononuclear iridium species.

Materials and Methods

All air and water sensitive procedures were carried out either in a Vacuum Atmosphere glove box under nitrogen (2-10 ppm $O_2$ for all manipulations) or using standard Schlenk techniques under nitrogen. Dichloromethane-d2, methanol-d4, D2O, and any other NMR solvents were purchased from Cambridge Isotopes Laboratories. Dichloromethane-d2 and methanol-d4 are carefully dried prior to use. Dichloromethane-d2 is stirred over $CaH_2$ for 1 day then vapor transferred into a dry flask; methanol-d4 is stirred over Na for 1 day then vapor transferred into a dry flask. Dichloromethane and hexanes are purchased from VWR and dried in a J. C. Meyer solvent purification system with alumina/copper(II) oxide columns; glycerol (EMD Millipore), $CDCl_3$ (Cambridge Isotopes), hydrochloric acid (VWR), and methanol (VWR) were used as received; vegetable oils were purchased from a local grocery store and used without purification; iridium complexes 1, 2, and 3 were synthesized using a previously reported method. 1,2 Lactic acid purification and lactide synthesis has been reported previously from our group.1 Iron complex 7 was prepared according to published procedure. (Chakraborty, S.; Dai, H.; Bhattacharya, P.; Fairweather, N. T.; Gibson, M. S.; Krause, J. A. Guan, H. J. Am. Chem. Soc., 2014, 136, 7869-7872).

NMR spectra were recorded on a Varian VNMRS 400, 500 or 600 spectrometer, processed using MestroNova. All chemical shifts are reported in units of ppm and referenced to the residual 1H or 13C solvent peak and line-listed according to (s) singlet, (bs) broad singlet, (d) doublet, (t) triplet, (dd) double doublet, etc. 13C spectra are delimited by carbon peaks, not carbon count. Air-sensitive NMR spectra were taken in 8" J-Young tubes (Wilmad or Norell) with Teflon valve plugs. X-ray crystallography data were obtained on a Bruker APEX DUO single-crystal diffractometer equipped with an APEX2 CCD detector, Mo fine-focus and Cu micro-focus X-ray sources.

Figure 5:
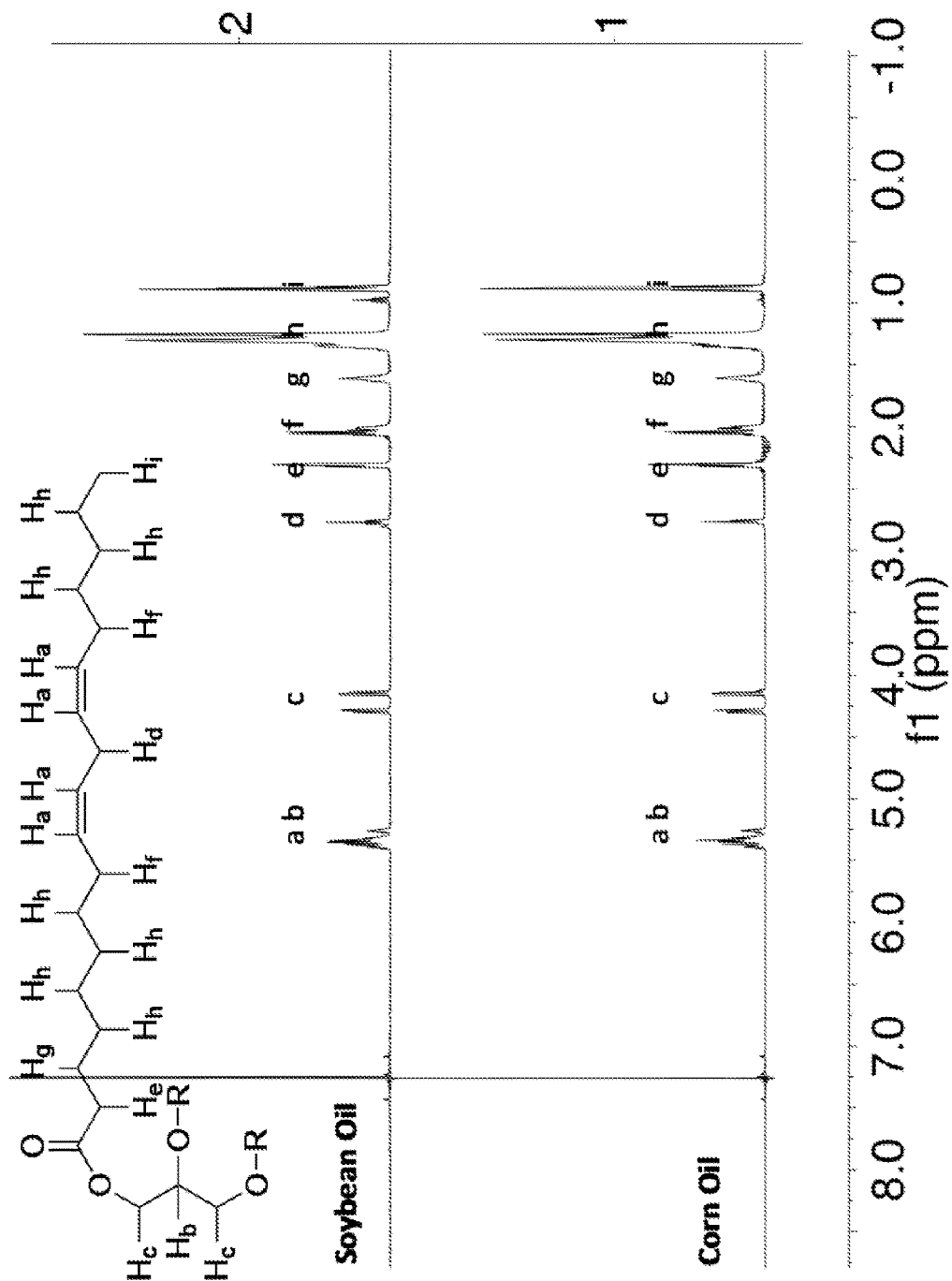
FIG. 5. $^1H$ NMR spectrum of soybean and corn oil at 25° C. in $CDCl_3$.

Reaction Procedures and Characterization Data
Characterization of Crude Vegetable Oils
FIG. 5 provides $^1H$ NMR spectra of soybean and corn oil at 25° C. in $CDCl_3$.

$^1H$ NMR (600 MHz, chloroform-d1) δ 5.35 (m, $H_a$ 8H), 5.26 (tt, J=6.0, 4.3 Hz, $H_b$ 1H), 4.29 (dd, J=11.9, 4.3 Hz, $H_c$ 2H), 4.14 (dd, J=11.9, 4.3 Hz, $H_c$ 1H), 2.77 (ddd, J=6.8, 1.2, 0.65 Hz, $H_d$ 3H), 2.31 (m, $H_e$ 1H), 2.04 (m, $H_f$ 11H), 1.61 (m, $H_g$ 6H), 1.30 (m, $H_h$ 1H), 0.88 (t, J=5.7 Hz, $H_i$ 1H).

Selective Reduction of Polyunsaturated Fatty Acids

Figure 6:
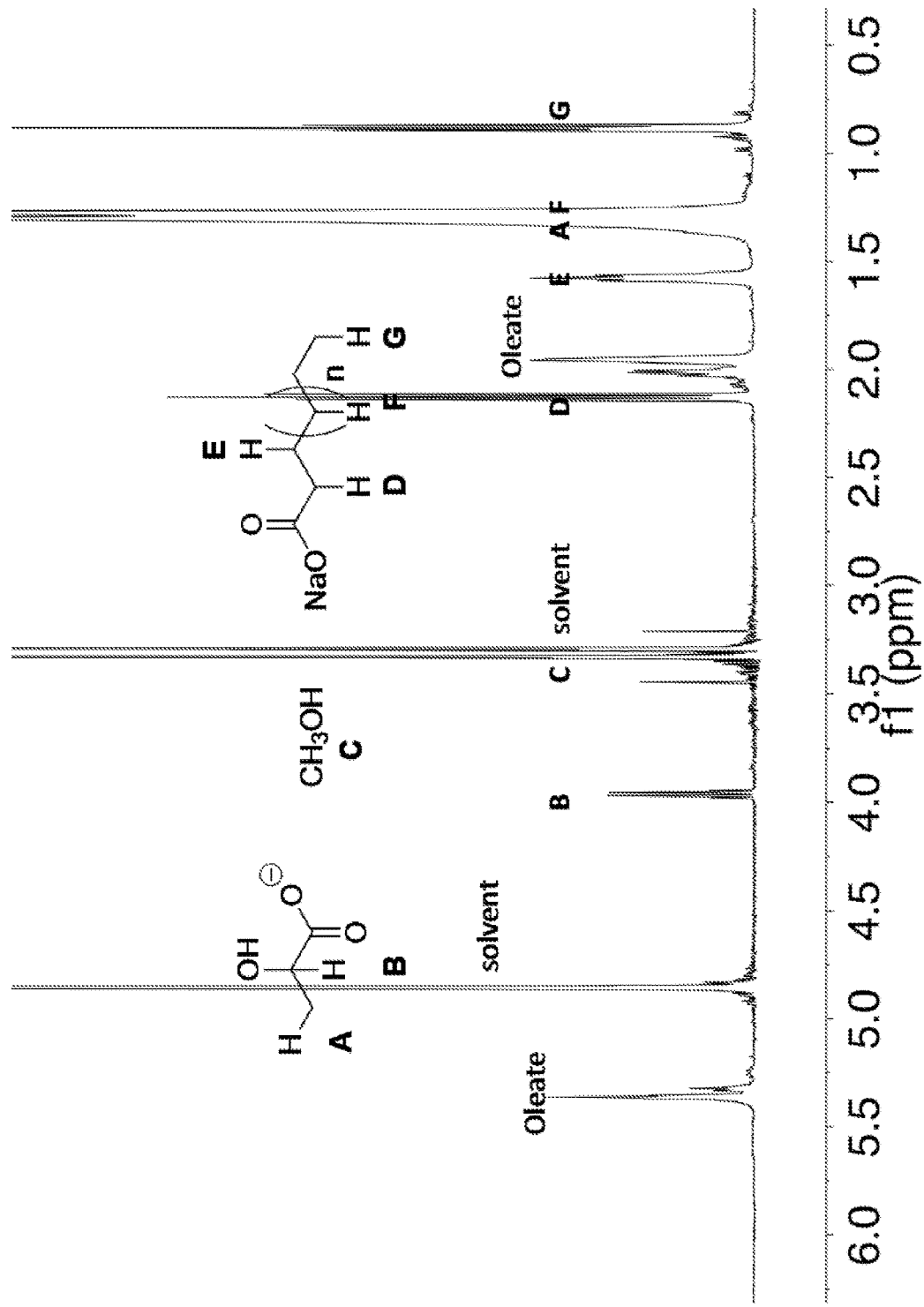
FIG. 6. A $^1H$ NMR snapshot at 25° C. of the reaction mixture by taking a small aliquot of the mixture in $CD_3OD$.

General procedure: The iridium catalysts for glycerol dehydrogenation are kept in a glovebox for long term storage. In a typical reaction, iridium catalyst 1 (1 mg, 0.3 mol %), base (i.e. KOH, NaOH), vegetable oil (0.5 mL) and additional reducing alcohol (i.e. CH3OH, glycerol) are measured as specified in the main text outside the glovebox, added to a thick-wall Schlenk bomb equipped with a magnetic stir bar. The reaction progress is monitored by 1H-NMR in methanol-d4. The crude reaction mixture is analyzed as shown in FIG. 6. An oil bath is used for heating the reaction; the temperature is monitored using an alcohol thermometer. Normally <±2.5° C. temperature fluctuation is observed.

Figure 7:
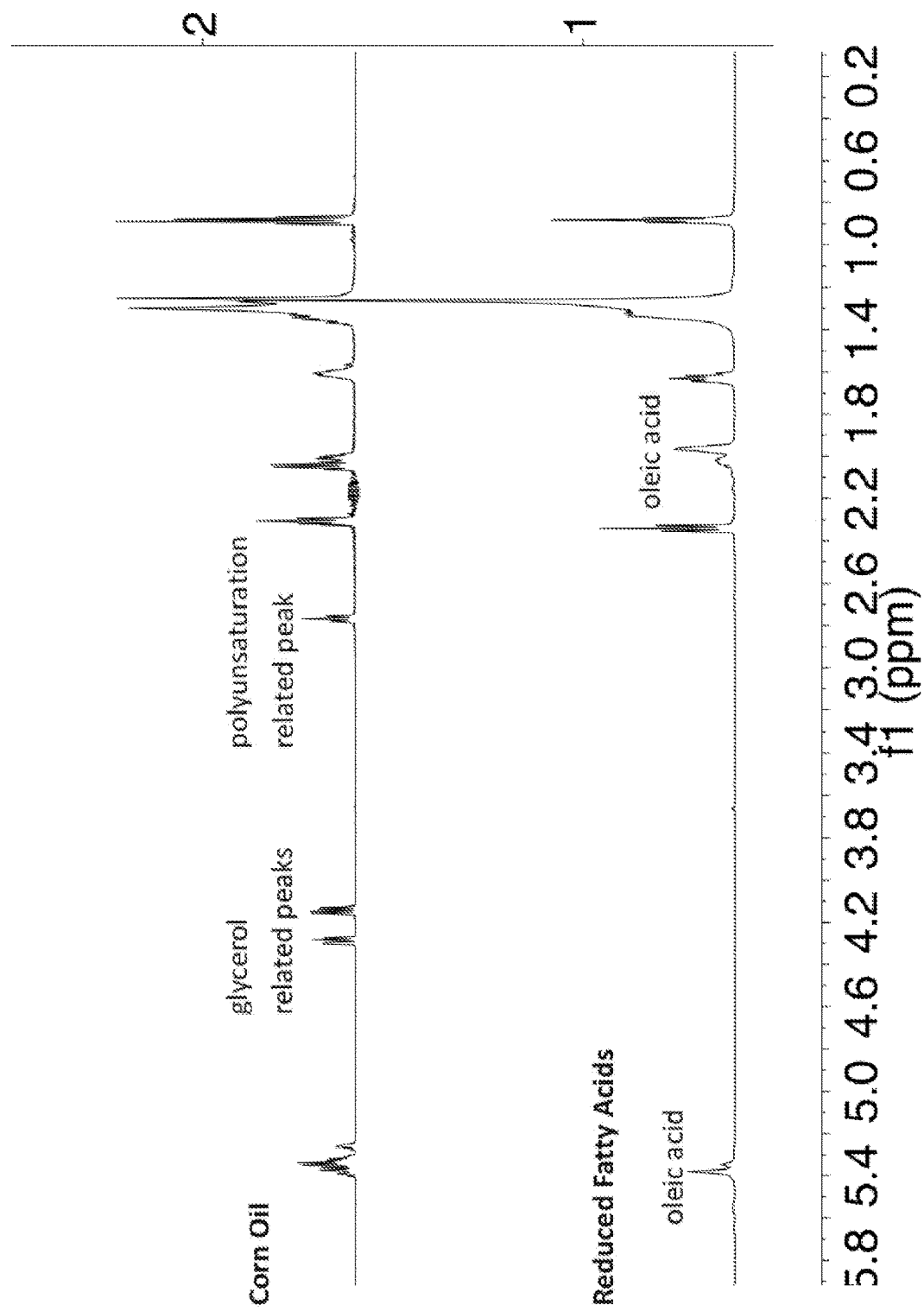
FIG. 7. Reduced fatty acids compared with corn oil by 1H NMR at 25° C. in $CDCl_3$.
Figure 8:
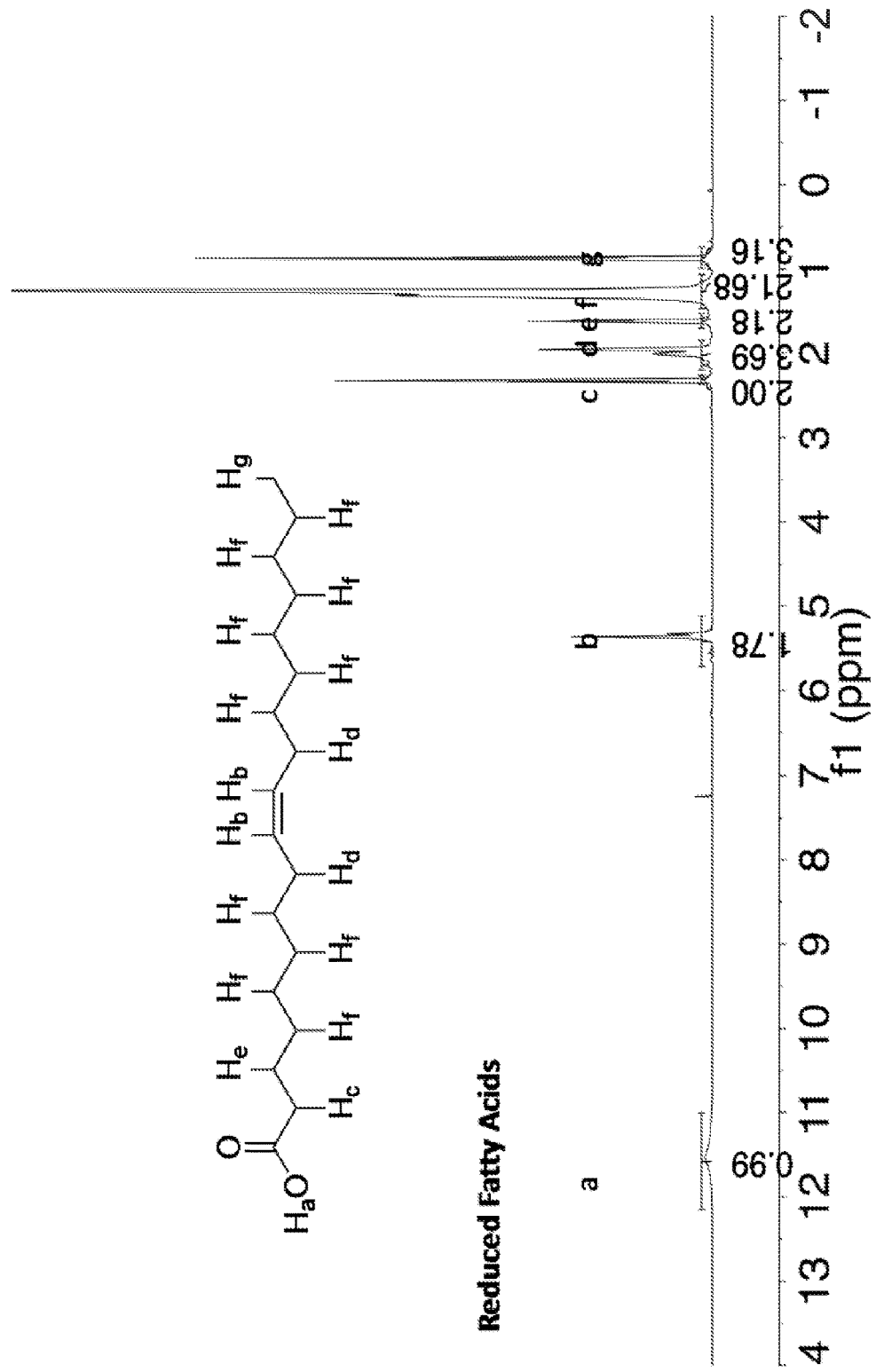
FIG. 8. $^1H$ NMR of reduced fatty acids at 25° C. in $CDCl_3$.

Purification of Reduced Fatty Acids
General procedure: to a mixture from the reaction above, conc. hydrochloric acid (37 w/w %, ca. 0.5 mL or 1.1 equiv. to NaOH) was added. The solution was extracted with dichloromethane (15 mL×3) to yield ca. 400 mg (90%) fatty acids as a pale yellow oil. 1H-NMR shows the fatty acids to be free from starting material, lactic acid, and glycerol (FIG. 7). The full $^1H$ NMR of reduced fatty acids is shown in FIG. 8.

$^1H$ NMR (600 MHz, chloroform-d3) δ 11.55 (s, $H_a$ 1H), 5.37 (m, $H_b$ 2H), 2.34 (t, J=7.5 Hz, $H_c$ 2H), 2.00 (m, $H_d$ 4H), 1.63 (tt, J=7.6, 7.4 Hz, $H_e$ 2H), 1.28 (m, $H_f$ 20H), 0.88 (t, J=5.8 Hz, $H_g$ 3H).

Figure 9:
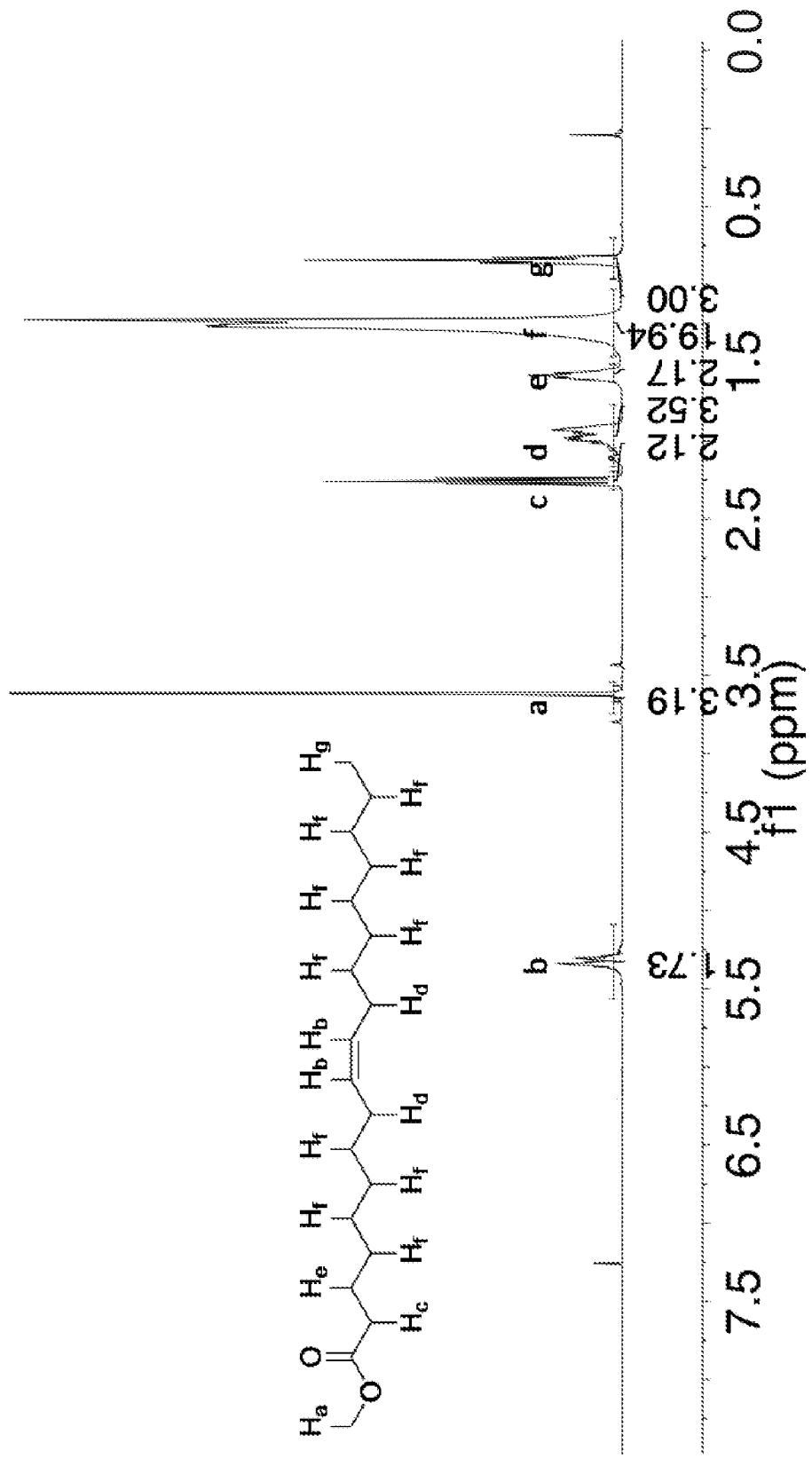
FIG. 9. $^1H$ NMR spectrum of FAMEs formed from reduced fatty acids at 25° C. in $CDCl_3$.
Figure 10:
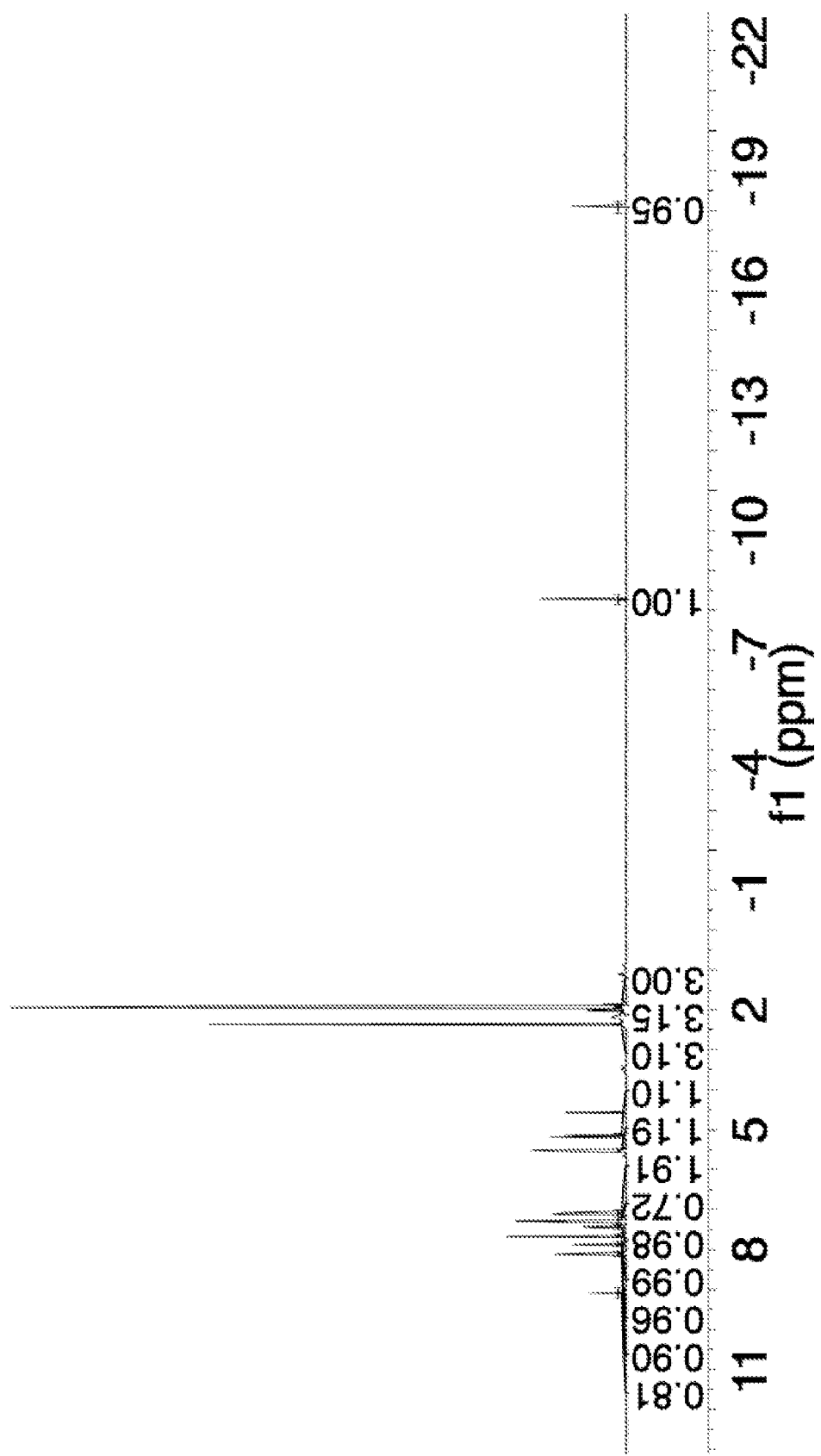
FIG. 10. $^1H$ NMR spectrum of iridium hydride complex 6 at 25° C. in $CD_3CN$
Figure 11:
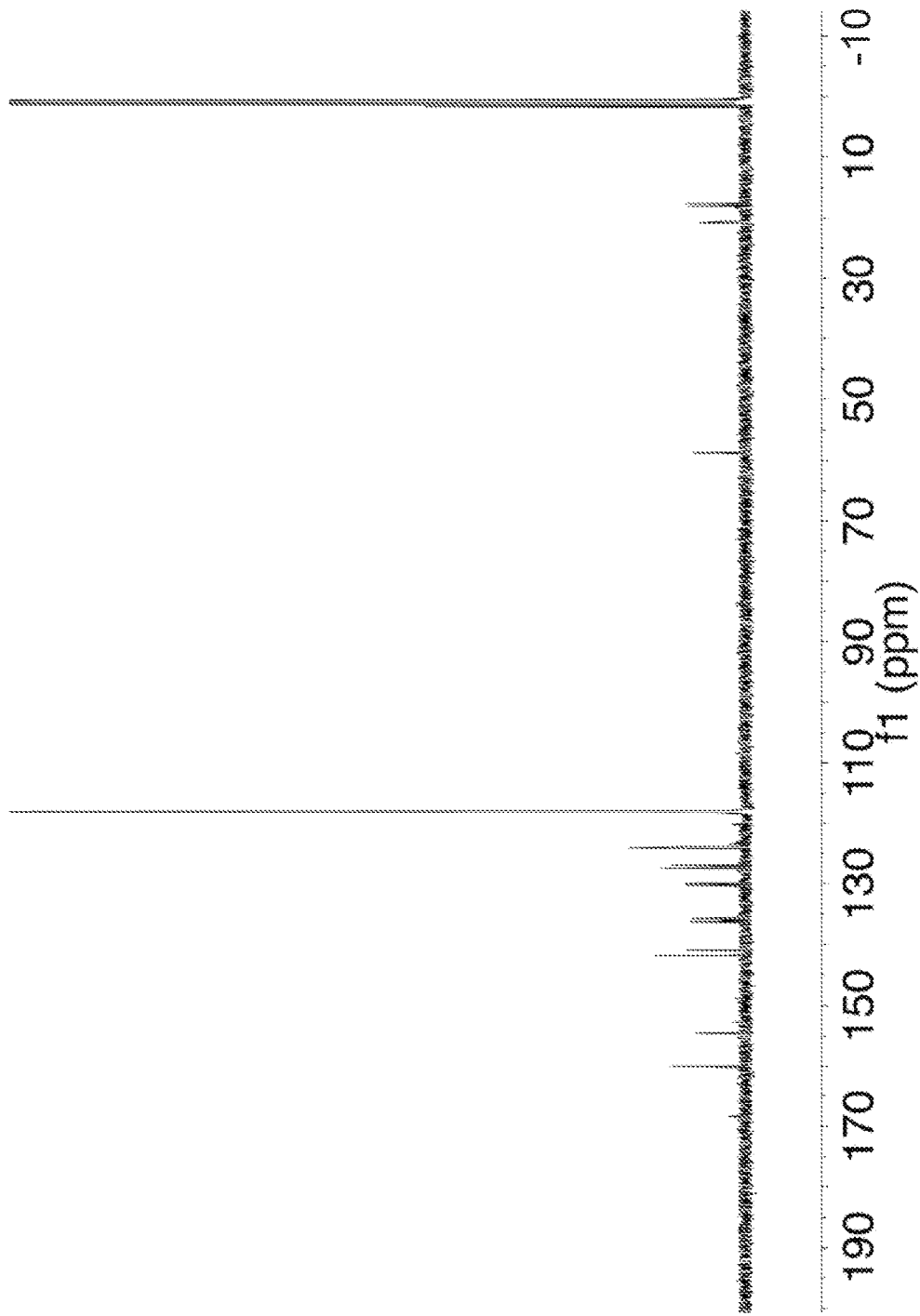
FIG. 11. $^{13}C$ NMR spectrum of iridium hydride complex 6 at 25° C. in $CD_3CN$.

Reduced Fatty Acids
FAME Synthesis
General procedure: 400 mg reduced fatty acids from the previous step is dissolved in 2 mL of methanol. To the fatty acid solution, 10 drops of concentrated sulfuric acid was added. The resulted solution is then refluxed for 2 hours. Extraction with ethyl acetate (15 mL×3) was performed and the organic phase was dried over sodium sulfate and dried under vacuum to yield ca. 300 mg (65% from triglyceride) fatty acid methyl esters (FAMEs). The purity of the product was examined by $^1H$ NMR as shown in FIG. 9.

$^1H$ NMR (400 MHz, chloroform-d3) δ 5.33 (m, $H_b$ 2H), 3.62 (s, $H_a$ 3H), 2.26 (t, J=7.6 Hz, $H_c$ 2H), 1.98 (m, $H_d$ 4H), 1.59 (m, $H_e$ 2H), 1.25 (m, $H_f$ 20H), 0.85 (t, J=5.8 Hz, $H_g$ 3H).

Separation of Glycerol and Lactic Acid
While the products can be separated by extraction, if methanol is used as the reductant; when glycerol is added to the reaction mixture as the reductant, products are most

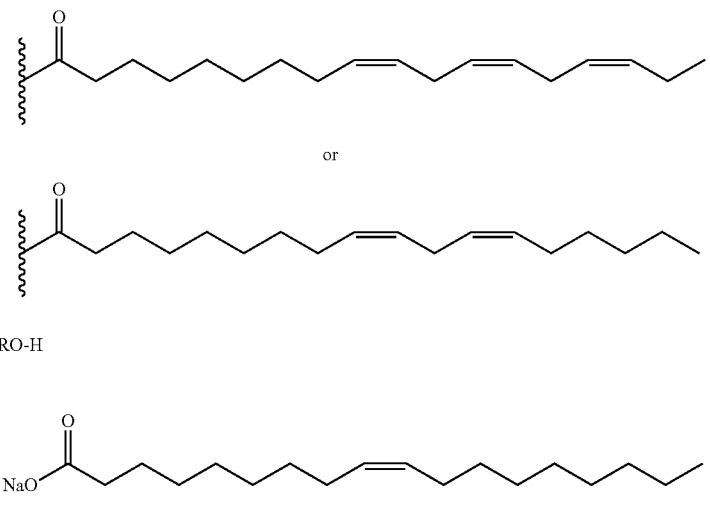

conveniently separated by ion exchange chromatography. General procedure: A solution containing glycerol, lactate, and other salt from the reduction of fatty acids reaction was passed through a column filled with ion-exchange resin (Amberlite) in OH-form. The fraction containing glycerol NaOH was collected by elution with DI water at neutral pH. The fraction containing lactic acid and HCl was collected at successive elution with 1 M HCl solution. Both fractions were separately neutralized by NaOH or HCl, evaporated to dryness and extracted with ethanol. Ethanol solutions of glycerol and Na-lactate were evaporated giving pure glycerol and Na-lactate.

Complex 6

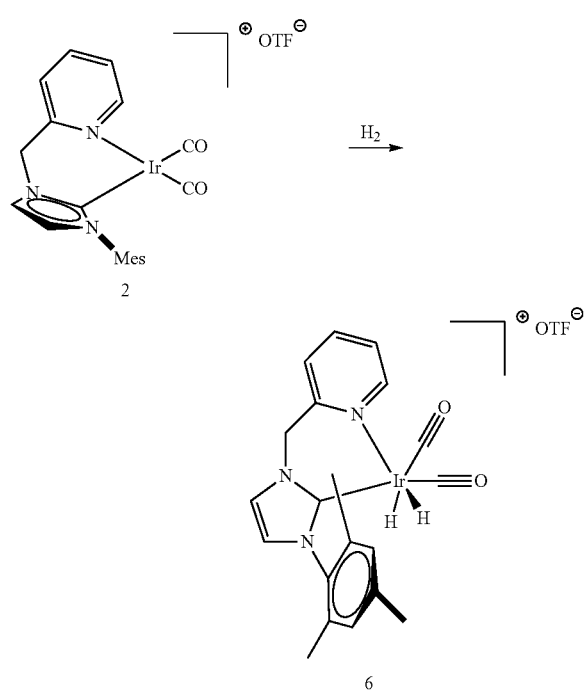

In the glovebox, iridium complex 2 (10 mg) was dissolved in 0.6 mL dry dicholoromethane-d2 or acetonitrile-d3 in a J. Young NMR tube. The solution was frozen in liquid nitrogen so that the atmosphere could be evacuated on the Schlenk line. The solution was then allowed to thaw at room temperature. The NMR tube was connected to 1 atm. $H_2$ gas. Reaction was facilitated by gently turning the tube upside down a few times. The reaction progress was monitor by 1H-NMR. After the reaction is finished, the solution was taken into the glovebox and poured into a small vial. On top of the solution, hexanes or diethyl ether, in case of dicholoromethane or acetonitrile respectively, was carefully layered. Over a few days, crystals grew at the bottom of the vial. These crystals appear to be NMR-pure iridium complex 6. Crystals grew from DCM/hexanes were used for X-ray crystallography.

$^1$H NMR (400 MHz, acetonitrile-d3) δ 9.10 (d, J=5.2 Hz, py 1H), 8.12 (tt, J=7.7, 1.4 Hz, py 1H), 7.87 (d, J=7.8 Hz, py 1H), 7.67 (t, J=1.6 Hz, mes 1H), 7.43 (dtt, J=7.7, 5.2, 1.4 Hz, py 1H), 7.29 (t, J=1.6 Hz, mes 1H), 7.11 (m, imi 1H), 7.09 (m, imi 1H), 5.52 (d, J=15.6 Hz, methylene 2H), 5.16 (d, J=15.6 Hz, methylene 2H), 2.36 (s, mesityl-para-methyl 3H), 1.95 (s, mesityl-ortho-3H), 1.91 (s, mesityl-ortho-3H), −8.28 (d, J=4.0 Hz, Ir—H, 1H), −18.11 (d, J=4.0 Hz, Ir—H, 1H).

$^{13}$C NMR (100 MHz, acetonitrile-d3) δ 160.00, 154.52, 141.76, 140.89, 136.24, 135.97, 135.66, 130.17, 129.88, 127.43, 126.94, 124.11, 123.88, 58.76, 20.85, 18.03, 17.61.

Crystal Structure Data

Figure 12:
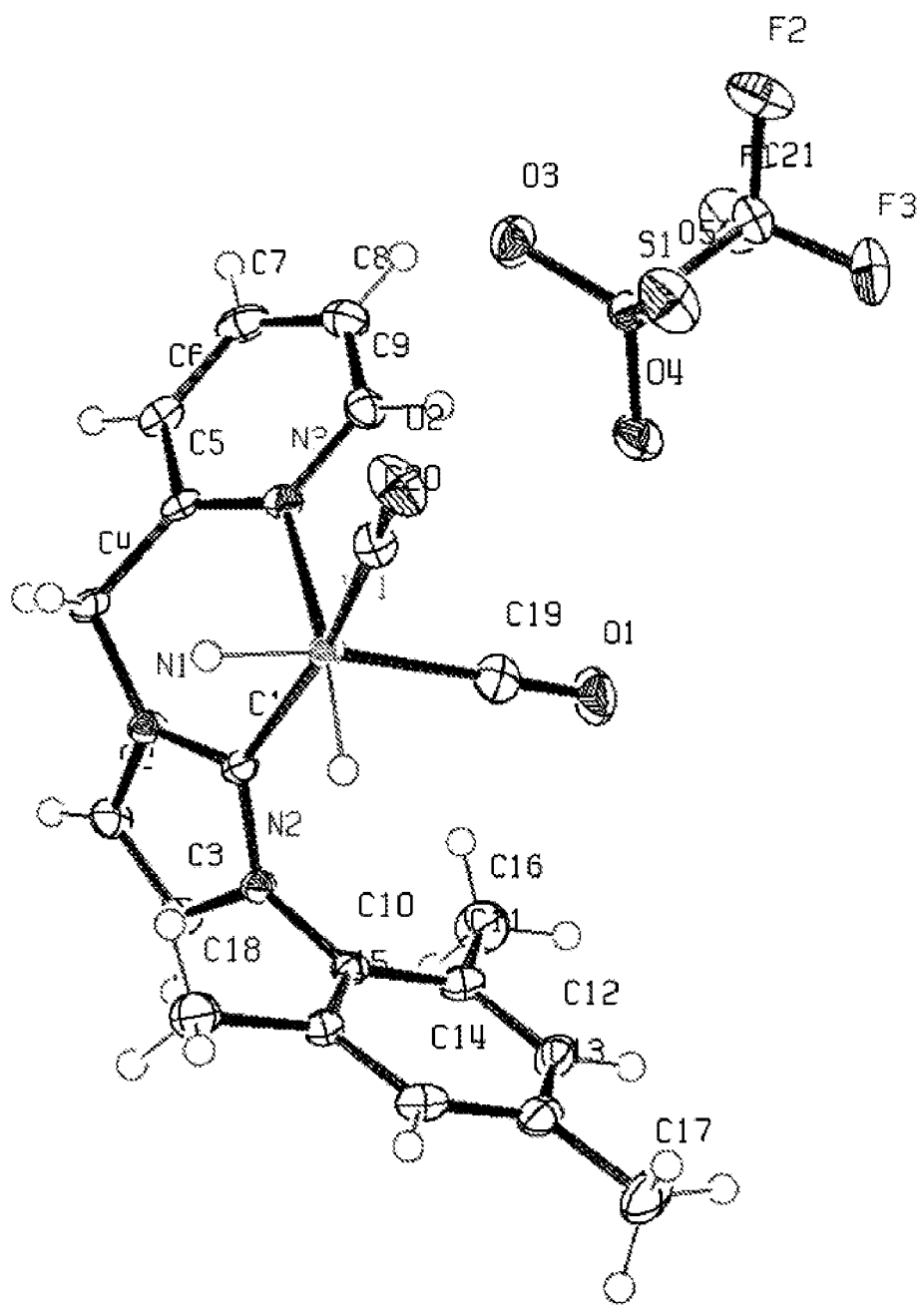
FIG. 12. ORTEP Diagram of Complex 6 with atom numbering

FIG. 12 provides ORTEP Diagram of Complex 6 with atom numbering. A specimen of C21H21F3IrN3O5 S was used for the X-ray crystallographic analysis. The X-ray intensity data were measured on a Bruker APEX DUO system equipped with a TRIUMPH curved-crystal monochromator and a MoKα fine-focus tube (λ=0.71073 Å)

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

REFERENCES (1) (a) Demirbas. *Biofuels* 2009, 319-329. (b) Lee, D. H.; Lee, D. J. In *Energy and Fuels*; 2008; Vol. 22, pp 177-181. (c) Oladosu, G. *Appl. Energy* 2012, 99, 85-96. (d) Fernandes, S. D.; Trautmann, N. M.; Streets, D. G.; Roden, C. A.; Bond, T. C. *Global Biogeochem. Cycles* 2007, 21, GB2019. (e) Kant, P.; Wu, S. *Environ. Sci. Technol.* 2011, 45, 7114-7115. (f) Cabral, F. J.; Cissé, F.; Diagne, A.; Siwa, M. *Econ. Bull.* 2017, 37 (3), 1435-1449.

(2) (a) Wu, X.; Leung, D. Y C. *Appl. Energy* 2011, 88 (11), 3615-3624. (b) Gupta, J.; Agarwal, M.; Dalai, A. K. *Biocatal. Agric. Biotechnol.* 2016, 8 (7), 112-120. (c) Sahoo, P. K.; Das, L. M. *Fuel* 2009, 88 (9), 1588-1594.

(3) (a) Demirbas, A. *Energy Convers. Manag.* 2008, 49 (8), 2106-2116. (b) Chupka, G. M.; Fouts, L.; McCormick, R. L. *Energy Environ. Sci.* 2012, 5 (9), 8734. (c) Chupka, G. M.; Yanowitz, J.; Chiu, G.; Alleman, T. L.; Mccormick, R. L. *J. Chem. Inf. Model.* 2013. (d) Chupka, G. M.; Fouts, L.; Lennon, J. A.; Alleman, T. L.; Daniels, D. A.; McCormick, R. L. *Fuel Process. Technol.* 2014, 118, 302-309.

(4) (a) Sharninghausen, L. S.; Mercado, B. Q.; Crabtree, R. H.; Hazari, N. *Chem. Commun.* 2015, 51, 16201-16204. (b) Sharninghausen, L. S.; Campos, J.; Manas, M. G.; Crabtree, R. H. *Nat. Commun.* 2014, 5, 5084. (c) Pagliaro, M.; Ciriminna, R.; Kimura, H.; Rossi, M.; Della Pina, C. *Angew. Chem. Int. Ed.* 2007, 46, 4434-4440. (d) Yang, F.; Hanna, M. A.; Sun, R. *Biotechnol. Biofuels* 2012, 5, 13.

(5) Lu, Z.; Demianets, I.; Hamze, R.; Terrile, N. J.; Williams, T. J. *ACS Catal.* 2016, 6, 2014-2017.

(6) Pimentel, D.; Patzek, T. *Nat. Resour. Res.* 2005, 14, 65-76.

(7) (a) Chuah, L. F.; Klemes, J. J.; Yusup, S.; Bokhari, A.; Akbar, M. M. *Clean Technol. Environ. Policy* 2017, 19, 859-868. (b) Mahmudul, H. M.; Hagos, F. Y; Mamat, R.; Adam, A. A.; Ishak, W. F. W.; Alenezi, R. *Renew. Sustain. Energy Rev.* 2017, 72, 497-509.

(8) (a) Thunyaratchatanon, C.; Luengnaruemitchai, A.; Chollacoop, N.; Yoshimura, Y *Fuel* 2016, 163, 8-16. (b) Zaccheria, F.; Psaro, R.; Ravasio, N. *Green Chem.* 2009, 11, 462. (c) Su, M.; Yang, R.; Li, M. In *Fuel* 2013, 103, 398-407. (d) Yang, R.; Su, M.; Li, M.; Zhang, J.; Hao, X.; Zhang, H. *Bioresour. Technol.* 2010, 101, 5903-5909. (e) Papadopoulos, C. E.; Lazaridou, A.; Koutsoumba, A.; Kokkinos, N.; Christoforidis, A.; Nikolaou, N. *Bioresour. Technol.* 2010, 101, 1812-1819. (f) Souza, B. S.; Pinho, D. M. M.; Leopoldino, E. C.; Suarez, P. A. Z.; Nome, F. *Appl. Catal. A Gen.* 2012, 433-434, 109-114.

(9) (a) Zhang, X.; Kam, L.; Trerise, R.; Williams, T. J. *Acc. Chem. Res.* 2017, 86-95. (b) Celaje, J. J. A.; Lu, Z.; Kedzie, E. A.; Terrile, N. J.; Lo, J. N.; Williams, T. J. *Nat. Commun.* 2016, 7, 11308. (c) Lu, Z.; Conley, B. L.; Williams, T. J. *Organometallics* 2012, 31, 6705-6714. (d) Lu, Z.; Williams, T. J. *Chem. Commun.* 2014, 50, 5391-5393. (e) Lu, Z.; Malinoski, B.; Flores, A. V; Conley, B. L.; Guess, D.; Williams, T. J. *Catalysts* 2012, 2, 412-421.

(10) Hamid, M. H. S. A.; Slatford, P. A.; Williams, J. M. J. *Adv. Synth. Catal.* 2007, 349, 1555-1575.

(11) (a) Gruber, S.; Neuburger, M.; Pfaltz, A. *Organometallics* 2013, 32, 4702-4711. (b) Chadwick, F. M.; Olliff, N.; Weller, A. S. J. *Organomet. Chem.* 2016, 812, 268-271.

(12) (a) Pfaltz, A.; Roseblade, S. J. *Acc. Chem. Res.* 2007, 40, 1402-1411. (b) Verendel, J., Pamies, O., Dieguez, M., Andersson, P. *Chem. Rev.* 2014, 114, 2130-2169.

What is claimed is:

1. A method extracting embedded hydrogen from glycerol or a compound containing functionalized glycerol, the method comprising:
    a) combining a glycerol-containing compound with a transition metal catalyst system to form a first composition, the transition metal catalyst system including a first organometallic complex having a transition metal M; and
    b) extracting hydrogen gas from the first composition or transferring hydrogen to an unsaturated hydrogen receptor that includes an unsaturated moiety to form a second composition.

2. The method of claim 1 wherein the glycerol-containing compound is free glycerol or a glyceride ester.

3. The method of claim 1 wherein the unsaturated moiety is C=C or C=O.

4. The method of claim 1 wherein the concentration of the glycerol-containing compound is from about 1 to a about 100 weight percent of the total weight of the first composition.

5. The method of claim 1 wherein the concentration of the unsaturated hydrogen receptor is from about 1 to a about 100 weight percent of the total weight of the first composition.

6. The method of claim 1 wherein steps a) and b) are performed at a reaction temperature from about 100 to 290 C.

7. The method of claim 1 wherein a $C_{2-3}$ carboxylate is formed by reaction of the glycerol-containing compound with the transition metal catalyst system.

8. The method of claim 7 wherein a lactate or acetate is formed by reaction of the glycerol-containing compound with the transition metal catalyst system.

9. The method of claim 1 wherein a salt that is formed by steps a) and b) is dissolved in an aqueous solution and the salt is crystallized from this solution.

10. The method of claim 9 wherein the salt is purified by passing through a resin.

11. The method of claim 1 wherein the glycerol-containing compound includes at least one unsaturated fatty acid group that has at least one degree of unsaturation such that the first composition includes a reactant fatty acid or reactant fatty acid salt resulting in the second composition including an ester of a fatty acid having a lower degree of unsaturation than the unsaturated fatty acid group in the glycerol-containing compound wherein hydrogen for reduction comes from the glycerol formed from the glycerol-containing compound.

12. The method of claim 11 wherein free fatty acids or fatty acid esters are isolated by aqueous extraction to remove impurities and afford pure fatty acid or fatty acid esters.

13. The method of claim 1 wherein the transition metal catalyst system further includes an iron-containing complex, the iron-containing complex being different than the first organometallic complex.

14. The method of claim 1 wherein the first composition further includes a base.

15. The method of claim 14 wherein the concentration of the base is from about 1 to about 100 weight percent of the total weight of the first composition.

16. The method of claim 1 wherein an acid is combined with the glycerol-containing compound and a first transition metal catalyst to form the second composition.

17. The method of claim 1 wherein the glycerol-containing compound is a vegetable oil.

18. The method of claim 1 wherein the second composition further includes an alcohol.

19. The method of claim 18 wherein the alcohol is methanol.

20. The method of claim 1 wherein the first composition further includes a lactide or polylactide.

21. The method of claim 1 wherein the transition metal M is beryllium, magnesium, aluminum, scandium, titanium, vanadium, chromium, manganese, iron, cobalt, nickel, copper, zinc, gallium, germanium, yttrium, zirconium, niobium, molybdenum, technetium, ruthenium, rhodium, palladium, silver, cadmium, indium, tin, antimony, lanthanum, cerium, praseodymium, neodymium, promethium, samarium, europium, gadolimium, terbium, dysprosium, holmium, erbium, thalium, ytterbium, lutetium, hafnium, tantalum, tungsten, rhenium, osmium, iridium, gold, platinum, thallium, lead, bismuth, polonium, thorium, protactinium, uranium, neptunium, or plutonium.

22. The method of claim 21 wherein the transition metal M is ruthenium, rhodium, or iridium.

23. The method of claim 21 wherein the transition metal M is iridium.

24. The method of claim 21 wherein the first organometallic complex has formula I:

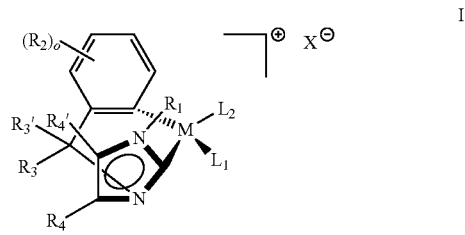

wherein:
  M is a transition metal;
  o is 0, 1, 2, 3, or 4;
  $R_1$ is a $C_{1-6}$ alkyl, a $C_{6-18}$ aryl, or an optionally substituted $C_{5-18}$ heteroaryl. In a refinement, $R_1$ is mesityl, methyl, ethyl, butyl, n-propyl, isopropyl, n-butyl, sec-butyl, or t-butyl;
  $R_2$ are independently an optionally substituted $C_{1-6}$ alkyl, halo, $NO_2$, an optionally substituted $C_{6-18}$ aryl, or an optionally substituted $C_{5-8}$ heteroaryl;
  $R_3$, $R_3'$ are independently hydrogen, an optionally substituted $C_{1-6}$ alkyl, halo, $NO_2$, an optionally substituted $C_{6-18}$ aryl, or an optionally substituted $C_{5-18}$ heteroaryl;

$R_4$, $R_4'$ are independently hydrogen, an optionally substituted $C_{1-6}$ alkyl, halo, $NO_2$, an optionally substituted $C_{6-18}$ aryl, or an optionally substituted $C_{5-18}$ heteroaryl, or an annulated aromatic ring; and $X^-$ is a negatively charge counter ion such as halide or trifluoromethanesulfonate (OTf); and $L_1$, $L_2$ are each independently a neutral ligand or a charged ligand.

25. The method of claim 21 wherein the first organometallic complex has formula VI:

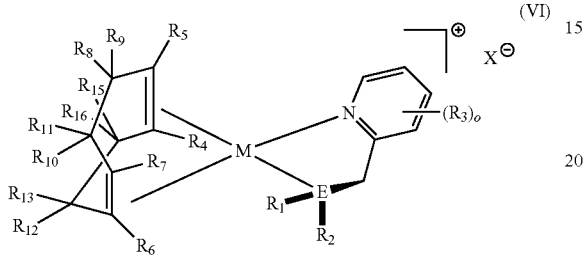

(VI)

wherein:

M is a transition metal;

E is P, N, or C (as in imidazolium carbene);

$R_1$, $R_2$ are each independently $C_{1-6}$ alkyl groups;

$R_3$ are each independently hydrogen, $C_{1-6}$ alkyl groups, $OR_{14}$, $NO_2$, or halogen;

o is 1, 2, 3, or 4;

$R_4$, $R_5$, $R_6$, $R_7$, $R_8$, $R_9$, $R_{10}$, $R_{11}$, $R_{12}$, $R_{13}$, $R_{15}$, $R_{16}$ are each independently hydrogen or $C_{1-6}$ alkyl groups;

$R_{14}$ is hydrogen or $C_{1-6}$ alkyl group; and $X^-$ is a negatively charge counter ion such as halide or trifluoromethanesulfonate (OTf).

26. The method of claim 21 wherein the first organometallic complex has formula VIII:

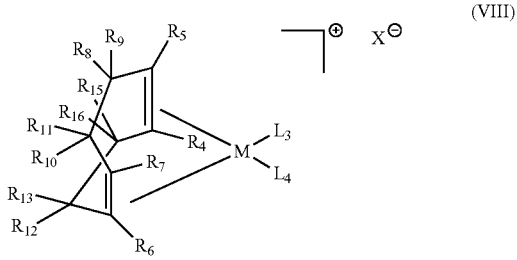

(VIII)

wherein:

M is a transition metal;

$R_4$, $R_5$, $R_6$, $R_7$, $R_8$, $R_9$, $R_{10}$, $R_{11}$, $R_{12}$, $R_{13}$, $R_{15}$, $R_{16}$ are each independently hydrogen or $C_{1-6}$ alkyl groups;

$X^-$ is a negatively charge counter ion such as halide or trifluoromethanesulfonate (OTf); and $L_3$, $L_4$ are each independently a neutral ligand.

27. The method of claim 21 wherein the first organometallic complex has formula IX:

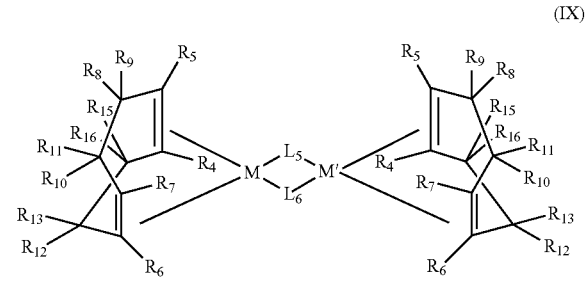

(IX)

wherein:

M, M' are each independently a transition metal where M and M' can be the same or different;

$R_4$, $R_5$, $R_6$, $R_7$, $R_8$, $R_9$, $R_{10}$, $R_{11}$, $R_{12}$, $R_{13}$, $R_{15}$, $R_{16}$ are each independently hydrogen or $C_{1-6}$ alkyl groups; and $L_5$, $L_6$ are each independently a bidentate ligand, a linking ligand, a neutral ligand, or an monoanionic ligand.

28. A method for forming a biodiesel fuel, the method comprising:

combining a triglyceride with a transition metal catalyst system to form a first composition that includes a reactant fatty acid or reactant fatty acid salt, the triglyceride including an unsaturated fatty acid group that has at least one degree of unsaturation, the transition metal catalyst system including a first organometallic complex having a transition metal M; and combining the first composition with an alcohol to form a second composition, the second composition including an ester of a fatty acid having a lower degree of unsaturation than the unsaturated fatty acid group in the triglyceride wherein hydrogen for reduction comes from glycerol formed from the triglyceride.

29. The method of claim 28 wherein the transition metal catalyst system further includes an iron-containing complex, the iron-containing complex being different than the first organometallic complex.

30. The method of claim 28 wherein a base is combined with the triglyceride with a first transition metal catalyst to form a first composition.

31. The method of claim 28 wherein an acid is combined with the triglyceride with a first transition metal catalyst to form a second composition.

32. The method of claim 28 wherein the triglyceride is a vegetable oil.

33. The method of claim 28 wherein the alcohol is methanol.

34. The method of claim 28 wherein the first composition further includes a lactide or polylactide.

35. The method of claim 28 wherein the transition metal M is beryllium, magnesium, aluminum, scandium, titanium, vanadium, chromium, manganese, iron, cobalt, nickel, copper, zinc, gallium, germanium, yttrium, zirconium, niobium, molybdenum, technetium, ruthenium, rhodium, palladium, silver, cadmium, indium, tin, antimony, lanthanum, cerium, praseodymium, neodymium, promethium, samarium, europium, gadolimium, terbium, dysprosium, holmium, erbium, thalium, ytterbium, lutetium, hafnium, tantalum, tungsten, rhenium, osmium, iridium, gold, platinum, thallium, lead, bismuth, polonium, thorium, protactinium, uranium, neptunium, or plutonium.

36. The method of claim 28 wherein the first organometallic complex has formula

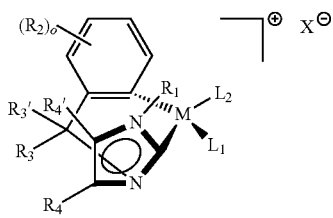

wherein:

M is a transition metal;

o is 0, 1, 2, 3, or 4;

$R_1$ is a $C_{1-6}$ alkyl, a $C_{6-18}$ aryl, or an optionally substituted $C_{5-18}$ heteroaryl, In a refinement, $R_1$ is mesityl, methyl, ethyl, butyl, n-propyl, isopropyl, n-butyl, sec-butyl, or t-butyl;

$R_2$ are independently an optionally substituted $C_{1-6}$ alkyl, halo, $NO_2$, an optionally substituted $C_{6-18}$ aryl, or an optionally substituted $C_{5-18}$ heteroaryl;

$R_3$, $R_3'$ are independently hydrogen, an optionally substituted $C_{1-6}$ alkyl, halo, $NO_2$, an optionally substituted $C_{6-18}$ aryl, or an optionally substituted $C_{5-18}$ heteroaryl;

$R_4$, $R_4'$ are independently hydrogen, an optionally substituted $C_{1-6}$ alkyl, halo, $NO_2$, an optionally substituted $C_{6-18}$ aryl, or an optionally substituted $C_{5-18}$ heteroaryl, or an annulated aromatic ring; and $X^-$ is a negatively charge counter ion such as halide or trifluoromethanesulfonate (OTf); and $L_1$, $L_2$ are each independently a neutral ligand or a charged ligand.

37. The method of claim 28 wherein the first organometallic complex has formula VI:

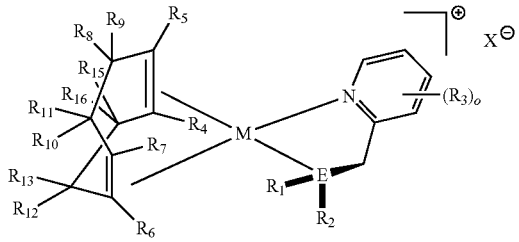

(VI)

wherein:

M is a transition metal;

E is P, N, or C (as in imidazolium carbene);

$R_1$, $R_2$ are each independently $C_{1-6}$ alkyl groups;

$R_3$ are each independently hydrogen, $C_{1-6}$ alkyl groups, $OR_{14}$, $NO_2$, or halogen;

o is 1, 2, 3, or 4;

$R_4$, $R_5$, $R_6$, $R_7$, $R_8$, $R_9$, $R_{10}$, $R_{11}$, $R_{12}$, $R_{13}$, $R_{15}$, $R_{16}$ are each independently hydrogen or $C_{1-6}$ alkyl groups;

$R_{14}$ is hydrogen or $C_{1-6}$ alkyl group; and $X^-$ is a negatively charge counter ion such as halide or trifluoromethanesulfonate (OTf).

38. The method of claim 28 wherein the first organometallic complex has formula VIII:

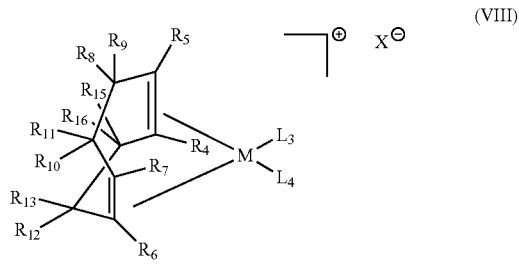

(VIII)

wherein:

M is a transition metal;

$R_4$, $R_5$, $R_6$, $R_7$, $R_8$, $R_9$, $R_{10}$, $R_{11}$, $R_{12}$, $R_{13}$, $R_{15}$, $R_{16}$ are each independently hydrogen or $C_{1-6}$ alkyl groups;

$X^-$ is a negatively charge counter ion such as halide or trifluoromethanesulfonate (OTf); and $L_3$, $L_4$ are each independently a neutral ligand.

39. The method of claim 28 wherein the first organometallic complex has formula IX:

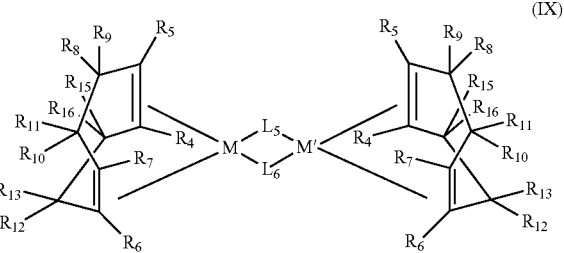

(IX)

wherein:

M, M' are each independently a transition metal where M and M' can be the same or different;

$R_4$, $R_5$, $R_6$, $R_7$, $R_8$, $R_9$, $R_{10}$, $R_{11}$, $R_{12}$, $R_{13}$, $R_{15}$, $R_{16}$ are each independently hydrogen or $C_{1-6}$ alkyl groups; and $L_5$, $L_6$ are each independently a bidentate ligand, a linking ligand, a neutral ligand, or an monoanionic ligand.

* * * * *

UNITED STATES PATENT AND TRADEMARK OFFICE
CERTIFICATE OF CORRECTION

Page 1 of 2

PATENT NO.           : 10,654,785 B2
APPLICATION NO.      : 16/193590
DATED                : May 19, 2020
INVENTOR(S)          : Travis J. Williams et al.

It is certified that error appears in the above-identified patent and that said Letters Patent is hereby corrected as shown below:

In the Claims

Column 19, Line 42, Claim 5:
After "hydrogen receptor is from about 1 to"
Delete "a".

Column 21, Line 5, Claim 24:
After "X⁻ is a negatively"
Delete "charge" and
Insert -- charged --.

Column 21, Line 40, Claim 25:
After "X⁻ is a negatively"
Delete "charge" and
Insert -- charged --.

Column 21, Line 65, Claim 26:
After "X⁻ is a negatively"
Delete "charge" and
Insert -- charged --.

Column 23, Line 36, Claim 36:
After "X⁻ is a negatively"
Delete "charge" and
Insert -- charged --.

Column 24, Line 11, Claim 37:
After "X⁻ is a negatively"
Delete "charge" and
Insert -- charged --.

Signed and Sealed this
Twelfth Day of January, 2021

Andrei Iancu
*Director of the United States Patent and Trademark Office*

CERTIFICATE OF CORRECTION (continued)
U.S. Pat. No. 10,654,785 B2

Column 24, Line 32, Claim 38:
After "X⁻ is a negatively"
Delete "charge" and
Insert -- charged --.